US011512102B2

(12) United States Patent
Conley et al.

(10) Patent No.: US 11,512,102 B2
(45) Date of Patent: Nov. 29, 2022

(54) ORGANOSILICON ON SOLID OXIDES, AND RELATED COMPLEXES, COMPOSITIONS, METHODS AND SYSTEMS

(71) Applicant: THE REGENTS OF THE UNIVERSITY OF CALIFORNIA, Oakland, CA (US)

(72) Inventors: Matthew P. Conley, Riverside, CA (US); Damien B. Culver, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 292 days.

(21) Appl. No.: 16/563,681

(22) Filed: Sep. 6, 2019

(65) Prior Publication Data

US 2020/0079802 A1    Mar. 12, 2020

Related U.S. Application Data

(60) Provisional application No. 62/727,995, filed on Sep. 6, 2018.

(51) Int. Cl.
| | | |
|---|---|---|
| *C07F 7/08* | (2006.01) | |
| *B01J 31/02* | (2006.01) | |
| *C07C 17/25* | (2006.01) | |
| *C07C 17/23* | (2006.01) | |

(52) U.S. Cl.
CPC ......... *C07F 7/0836* (2013.01); *B01J 31/0274* (2013.01); *C07C 17/23* (2013.01); *C07C 17/25* (2013.01); *B01J 2231/14* (2013.01); *B01J 2231/543* (2013.01); *B01J 2531/26* (2013.01); *B01J 2531/31* (2013.01); *B01J 2531/48* (2013.01); *B01J 2531/64* (2013.01)

(58) Field of Classification Search
CPC . C07F 7/836; C07F 7/36; C07C 17/23; C07C 17/25
See application file for complete search history.

(56) References Cited

U.S. PATENT DOCUMENTS

| | | | |
|---|---|---|---|
| 6,316,553 B1 | 11/2001 | McDaniel et al. | |
| 10,407,347 B2 * | 9/2019 | Boyle | B01J 13/06 |

OTHER PUBLICATIONS

Ahrens, et al., "Catalytic Hydrodefluorination of Fluoromethanes at Room Temperature by Silylium-ion-like Surface Species" *Chem. Int. Ed.*2013, 52, 5328-5332.
Beckett, et al. "Lewis acidity of tris(pentaflurophenyl)borane: crystal and molecular structure of B(C6F5)3-OPEt3" *Inorg. Chem. Commun.*2000, 3, 530-533.
Breneman, et al., "Determining Atom-Centered Monopoles from Molecular Electrostatic Potentials. The Need for High Sampling Density in Formamide Conformational Analysis" *J. Comput. Chem.*, 11, 361-373,1990.
Chirlian L.E. et al., "Atomic Charges Derived from electrostatic Potentials: A Detailed Study" *Comput. Chem.*, 6, 894-905,1987.
Comas-Vives, et al., "Carbon-Carbon Bond Formation by Activation of CH3F on Alumina" *J. Phys. Chem.*C2015, 119, 7156-7163.
Comas-Vives, et al. "Cooperativity between AI Sites Promotes Hydrogen Transfer and Carbon-Carbon Bond Formation upon Dimethyl Ether Activation on Alumina" *ACS Cent. Sci.*2015, 1, 313-319.
Conley, et al. "Heterolytic Activation of C—H Bonds on CrIII—O Surface Sites is a Key Step in Catalytic Polymerization of Ethylene and Dehydrogenation of Propane" *Inorg. Chem.*2015, 54, 5065-5078.
Conley, et al. "Polymerization of Ethylene by Silica-Supported Dinuclear CrIII Sites through and Initiation Step Involving C—H Bond Activation" *Angew. Chem. Int. Ed.*2014, 53, 1872-1876.
Coperet, C. "C—H Bond Activation and Orgnometallic Intermediates on Isolated Metal Centers on Oxide Surfaces" *Chem. Rev.*2010, 110, 656-680.
Culver, et al., "Activation of C—F Bonds by Electrophilic Organosilicon Sites Supported on Sulfated Zirconia", *Angewandte Chemie, International ed.*, 57 (45),2018, 14902-14905.
Culver, et al., "Generation of a well-defined electrophilic silicon center for hydrodefluorination", 19 pages.
Großekappenberg et al. "Quantitative Assessment of the Lewis Acidity of Silylium Ions" *Organometallics*2015, 34, 4952-4958.
Gu, et al. "Benzene Selectivity in Competitive Arene Hydrogenation: Effects of Single-Site Catalyst-Acidic Oxide Surface Binding Geometry" *J. Am. Chem. Soc.*2015, 137, 6770-6780.
Hirshfeld, "Bonded-Atom Fragments for Describing Molecular Charge Densities" *Theor. Chim. Act.*, 44, 129-38,1977.
Hu, et al. "Selective propane dehydrogenation with single-site CoII on SiO2 by a non-redox mechanism" *J. Catal.*2015, 322, 24-37.
IUPAC Periodic Table of the Elements dated Nov. 28, 2016 https://iupac.org/wp-content/uploads/2015/07/IUPAC_Periodic_Table-28Nov16.pdf.
Klare, et al. "Silylium ions in catalysis" *Royal Society of Chemistry*,2010, 39, 9176-9184.
Klet, et al. "Evidence for Redox Mechanisms in Organometallic Chemisorption and Reactivity on Sulfated Metal Oxides" *J. Am. Chem. Soc.*2018, 140, 6308-6316.
Krahl, T.; "Aluminium fluoride—the strongest solid Lewis acid: structure and reactivity" *Cat. Sci. Tech.*2017, 7, 773-796.
Liberman-Martin, A et al. Lewis Acidity of Bis(perfluorocatecholato)silane: Aldehyde Hydrosilylation Catalyzed by a Neutral Silicon Compound) *J. Am. Chem. Soc.*2015, 137, 5328-5331.

(Continued)

*Primary Examiner* — Pancham Bakshi
(74) *Attorney, Agent, or Firm* — Steinfl + Bruno LLP

(57) ABSTRACT

Organosilicon Lewis acids supported on activated oxides and metal oxo complexes grafted on the organosilicon Lewis acids as heterogeneous catalysts and the related compositions, methods and systems are described. These organosilicon Lewis acids and the grafted metal oxo complexes catalyze industrially important chemical reactions including, respectively, C—F bond activation and olefin metathesis reactions such as homocoupling and polymerizations.

16 Claims, 33 Drawing Sheets

(56) References Cited

OTHER PUBLICATIONS

Marenich, et al., "Charge Model 5: An Extension of Hirshfeld Population Analysis for the Accurate Description of Molecular Interactions in Gaseous and Condensed Phases" *J. Chem. Theory Comput.*,8, 527,2012.

Osegovic, et al. "A Solid Acidity Scale Based on the 31P MAS-NMR Shift of Chemisorbed Triethylphosphine Oxide" *J. Catal.* 1999, 182, 1-4.

Reed, et al., C. A. "H+, CH3+, and R3Si+ Carborane Reagents: When Triflates Fail" *Acc. Chem. Res*.2010, 43, 121-128.

Reed, et al., "Natural population analysis" *J. Chem. Phys.*,83, 2, 735-746,1985.

Reed, et al. "The Silylium Ion Problem, R3Si+ Bridging Organic and Inorganic Chemistry" *Acc. Chem. Res*.1998, 31, 325-332.

Rezisha, et al. "Bis(perchlorocatecholato)silane—A Neutral Silicon Lewis Super Acid" *Angew. Chem. Int. Ed*.2013, 57, 1717-1720.

Schweitzer, et al. "Propylene Hydrogenation and Propane Dehydrogenation by a Single-Site Zn2+ on Silica Catalyst" *ACS Catal.* 2014, 4, 1091-1098.

Scott et al. "Room-Temperature Catalytic Hydrodefluorination of C(sp3)-F Bonds" *J. Am. Chem. Soc*.2005, 127, 2852-2853.

Searles et al. "Silica-supported isolated gallium sites as highly active, selective and stable propane dehydrogenation catalysts" *Chem. Sci*.2017, 8, 2661-2666.

Shao, B.; et al. "Arylation of hydrocarbons enabled by organosilicon reagents and weakly coordinating anions" *Science*2017, 355, 1403-1407.

Stalzer, et al., "Single-Face/All-cis Arene Hydrogenation by a Supported Single-Site d0 Organozirconium Catalyst" *Angew. Chem.* 2016, 128, 5349-5353.

Stalzer, M.; "Supported Single-Site Organometallic Catalysts for the Synthesis of High-Performance Polyolefins" *Catal. Lett*.2015, 145, 3-14.

Tafazolian, et al. "A Well-Defined Ni(II) α-Diimine Catalyst Supported on Sulfated Zirconia for Polymerization Catalysis." *Organometallics*2017, 36, 2385-2388.

Valla, et al. "Role of Tricoordinate Al Sites in CH3ReO3/Al2O3 Olefin Metathesis Catalysts" *J. Am. Chem. Soc*.2016, 138, 6774-6785.

Weigend, et al., "Balanced basis sets of split valence, triple zeta valence and quadruple zeta valence quality for H to Rn: Design and assessment of accuracy" *Phys. Chem. Chem. Phys.*, 7, 3297-3305,2005.

Williams, et al. "Surface structural-chemical characterization of a single-site d0 heterogenous arene hydrogenation catalyst having 100% active sites" *Proc. Nat. Acad. Sci. USA*2013, 110, 413-418.

Wischert et al. "Dinitrogen: a selective probe for tri-coordinate Al "defect" sites on alumina" *Chem. Comm.* 2011, 47, 4890-4892.

Wischert, et al. "Optimal Water Coverage on Alumina: A Key to Generate Lewis Acid-Base Pairs that are Reactive Towards the C—H Bond Activation of Methane" *Chem. Int. Ed*.2011, 50, 3202-3205.

Wischert, et al. "γ-Alumina: The Essential and Unexpected Role of Water for the Structure, Stability, and Reactivity of "Defect" Sites" *J. Am. Chem. Soc*.2012, 134, 14430-14449.

Xie, et al. "Approaching the Silylium (R3Si+) Ion: Trends with Hexahalo (Cl, Br, I) Carboranes as Counterions" *J. Am. Chem. Soc*.1996, 118, 2922-2928.

Zapilko, et al. "Size-Selective Surface Silylation of Cagelike Mesoporous Silica SBA-2 with Disilazane Regents" *Chem. Mater*.2006, 18, 1479-1482.

Zheng, et al., "Minimally augmented Karlsruhe basis sets" *Theor. Chem. Acc.*, 128, 295-305,2011.

Ahrens, et al., "Catalytic Hydrodefluorination of Fluoromethanes at Room Temperature by Silylium-ion-like Surface Species" *Angew. Chem.* Apr. 2013, 125, 5346-5440.

Bahr, et al., "Electrophilic Aromatic Substitution with Silicon Electrophiles: Catalytic Friedel-Crafts C—H Silylation" *Angew. Chem. Int. Ed.* Jan. 2017, 56, 52-59.

Conley, et al, "Polymerization of Ethylene by Silica-Supported Dinuclear CrIII Sites through an Initiation Step Involving C—H Bond Activation" *Angew. Chem.* Jan. 2014, 126, 1903-1907.

Conley, et al., "Mesostructured Hybrid Organic-Silica Materials: Ideal Supports for Well-Defined Heterogeneous Organometallic Catalysts" *ACS Catalysis* Mar. 2014, 4, 1458-1469.

Copéret, et al., "Surface Organometallic and Coordination Chemistry toward Single-Site Heterogeneous Catalysts: Strategies, Methods, Structures, and Activities" *Chem. Rev.* Jan. 2016, 116, 323-421.

Corma, et al., "Lewis Acids: From Conventional Homogeneous to Green Homogeneous and Heterogeneous Catalysis" *Chem. Rev.* Oct. 2003, 103, 4307-4365.

Culver, et al., "A Bulky Pd(II) α-Diimine Catalyst Supported on Sulfated Zirconia for the Polymerization of Ethylene and Copolymerization of Ethylene and Methyl Acrylate" *Organometallics* Feb. 2018, 37, 1001-1006.

Delley, et al., "Local Structures and Heterogeneity of Silica-Supported M(III) Sites Evidenced by EPR, IR, NMR, and Luminescence Spectroscopies" *J. Am. Chem. Soc.* Jun. 2017, 139, 8855-8867.

Delley, et al., "Proton transfers are key elementary steps in ethylene polymerization on isolated chromium(III) silicates" *Proc. Nat. Acad. Sci. USA* Aug. 2014, 111, 32, 11624-11629.

Douvris, et al., "Hydrodefluorination and Other Hydrodehalogenation of Aliphatic Carbon-Halogen Bonds Using Silylium Catalysis" *J. Am. Chem. Soc.* Mar. 2010, 132, 4946-4953.

Douvris, et al. "Hydrodefluorination of Perfluoroalkyl Groups Using Silylium-Carborane Catalysts" *Science* Aug. 2008, 321, 1188-1190.

Duttwyler, et al., "C—F Activation of Fluorobenzene by Silylium Carboranes: Evidence for Incipient Phenyl Cation Reactivity" *Angew. Chem. Int. Ed.* Sep. 2010, 49, 7519-7522.

Grimme, et al., "A consistent and accurate ab initio parametrization of density functional dispersion correction (DFT-D) for the 94 elements H—Pu" *J. Chem. Phys.*, Apr. 2010, 132, 154104-1 to 154104-19.

Kemnitz, et al., "Amorphe Metallfluoride mit außergewöhnlich großer spezifischer Oberfläche" *Angew. Chem.* Jun. 2003, 115, 4383-4386 (German + corresponding English Publication).

Kemnitz, et al., "Amorphous Metal Fluorides with Extraordinary High Surface Areas" *Angew. Chem. Int. Ed.* Jun. 2003, 42, 4251-4254.

Mayer, et al., "The acceptor number—A quantitative empirical parameter for the electrophilic properties of solvents" *Chem.* Jan. 1975, 106, 1235-1257.

Mulliken, "Electronic Population Analysis on LCAO—MO Molecular Wave Functions" *J. Chem. Phys.* Oct. 1955, vol. 23, No. 10, 1833-1840.

Olah, et al., "Fluorinationswith Pyridinium Polyhydrogen Fluoride Reagent: 1-Fluoroadamantane" *Org. Synth.* Jan. 1978, 58, 75.

Román-Leshkov, et al., "Activation of Carbonyl-Containing Molecules with Solid Lewis Acids in Aqueous Media" *ACS Catal.* Sep. 2011, 1, 1566-1580.

Sattler, et al., "Catalytic Dehydrogenation of Light Alkanes on Metals and Metal Oxides" *Chem. Rev.* Aug. 2014, 114, 10613-10653.

Singh, et al., "An approach to computing electrostatic charges for molecules" *J. Comp. Chem.* Jan. 1984, vol. 5, No. 2, 129-145.

Wischert, et al., "Optimal Water Coverage on Alumina: A Key to Generate Lewis Acid-Base Pairs that are Reactive Towards the C—H Bond Activation of Methane" *Angew. Chem.* Jan. 2011, 123, 3260-3263.

Bekyarova E. "The coordination chemistry of oxide and nanocarbon materials" *Dalton Trans*, vol. 51, May 2022, pp. 8557-8570.

Witzke R. et al., "Nontraditional Catalyst Supports in Surface Organometallic Chemistry" *ACS Catal.* vol. 10, Sep. 2020, pp. 11822-11840.

\* cited by examiner

Table 1. Lewis Acidity of Silicon Lewis Acids Using the Guttman-Beckett Method.

| Compound | $\delta^{31}P$ | $\Delta\delta$ | ref |
|---|---|---|---|
| 1[a] | 93 | 43 | Present disclosure |
|  | 70 | 20 |  |
| Si(cat$^F$)$_2$[b] | 86.6 | 35.9 | 18 |
| Si(cat$^{Cl}$)$_2$[b] | 84.6 | 33.9 | 19 |
| [Et$_3$Si][c] | 88.6 | 42.4 | 20 |

[a] – solid-state (physisorbed); $d^{31}P(O=PEt_3)$ = 50 ppm[17]; [b] – CD$_2$Cl$_2$ solution; $d^{31}P(O=PEt_3)$ = 50.7; [c] – anion = [B(C$_6$F$_5$)$_4$]; C$_6$D$_6$ solution; $d^{31}P(O=PEt_3)$ = 46.4 ppm.

Figure 14

Table 2. Hydrodefluorination reactions catalyzed by 1.[a]

| Entry | Cat. | Substrate | $n_{substrate}$ (mmol) | $n_{cat}$ (μmol)[b] | t (h) | Conv (%) | TON[c] |
|---|---|---|---|---|---|---|---|
| 1 | 1 | $C_6H_5CF_3$ | 0.5 | 1 | 12 | 42 | 680 |
| 2[d] | 1 | $C_6F_5CF_3$ | 0.2 | 2.4 | 504 | 56 | 190 |
| 3[e] | 1 | $C_{10}H_{15}F$ | 0.4 | 1 | 24 | >99 | 340 |
| 4 | 2 | $C_6H_5CF_3$ | 0.5 | 3.4 | 12 | 0 | 0 |
| 5 | 3 | $C_6H_5CF_3$ | 0.5 | 13 | 24 | 0 | 0 |

[a] – Reactions at 80 °C with neat substrate and Et₃SiH at 80 °C; [b] – active silicon in 1 and total silicon in 2 and 3; [c] – mol Et₃SiF/mol active Si determined by ¹⁹F NMR and GC analysis; [d] – reaction run at 120 °C; [e] – reaction run at 25 °C.

(IX)

Table 4. Metathesis Activity of Catalyst (TIPSi-SZO$_{300}$-Mo1 0.028 mol%) in an Open Vial, Neat at RT

| TIPSi-SZO$_{300}$-Mo1 0.028 mol% (3515 equiv of 1-decene) | | | |
|---|---|---|---|
| Reaction Time | Conversion % | TOF$^a$ (h$^{-1}$) | %E: %Z |
| 2 min | 3.1% | 1664 | 69:31 |
| 4 min | 4.6% | 1250 | 75:25 |
| 6 min | - | - | - |
| 8 min | 7.7% | 1059 | 80:20 |
| 10 min | 9.2% | 1008 | 80:20 |
| 15 min | - | - | - |
| 20 min | 16.2% | 890 | 79:21 |
| 25 min | 18.9% | 833 | 79:21 |
| 30 min | - | - | - |
| 1 h | 22.9% | 419 | 82:17 |
| 2 h | 25.4% | 232 | 80:20 |
| 6 h | 41% | 24 | 79:21 |
| 24 h | 67% | 57 | 66:34 |

$^a$TOF = turnover frequency in (mol 1-decene)×(mol Mo)$^{-1}$×h$^{-1}$.

ORGANOSILICON ON SOLID OXIDES, AND RELATED COMPLEXES, COMPOSITIONS, METHODS AND SYSTEMS

CROSS REFERENCE TO RELATED APPLICATIONS

The present application claims priority to U.S. Provisional Application No. 62/727,995, entitled "Generation of Electrophilic Silicon Sites on Oxides for Catalytic Bond Activation" filed on Sep. 6, 2018 with the content of which is incorporated herein by reference in its entirety.

STATEMENT OF GOVERNMENT GRANT

This invention was made with government support under CHE1800561 awarded by the National Science Foundation. The government has certain rights in the invention.

FIELD

The present disclosure relates to organosilicon compounds, and their uses as catalysts. More particularly, the present disclosure relates to organosilicon on metal oxides and related complexes, compositions, methods and systems, which in several embodiments can be used to catalyze reactions with high activation energy.

BACKGROUND

Catalysis of reactions has been a central issue to be solved in several fields of chemistry, with particular references to catalysis of reactions involving selective breaking of bonds such as C=C double bonds, C—F bonds in organic substrate.

Despite progresses in the field, development of catalysts for reactions involving selective C—F activation, olefins metathesis or polymerization, remains a challenge.

SUMMARY

Described herein are organosilicon on metal oxides and related complexes, compositions, methods and systems, which in several embodiments allow selective catalysis of organic chemical transformations.

According to a first aspect, a solid organosilicon compound is described having Formula (I)

$$[M^1{}_mO_{o1}Si^1(R^1R^2R^3)L_{q/z}]\ [M^2O_{o2}Si^2(R^1R^2R^3)]_x \quad (I)$$

wherein
M$^1$ and M$^2$ are an element having an oxidation state of +p, wherein p ranges from 2 to 5,
Si$^1$ is a Lewis acidic silicon connected to M$^1$ via an oxygen, wherein other atoms in the solid organosilicon compound are represented stoichiometrically in relation to Si$^1$,
q represents a charge for M$^1{}_mO_{o1}Si^1(R^1R^2R^3)$, wherein q ranges from 1 to 3,
L is a counter anion bounded to M$^1$ and has a negative charge of −z, wherein z ranges from 1 to 3,
Si$^2$ represents a silicon bounded to M$^2$ via an oxygen and is at least two atoms spaced apart from L,
m is number of M$^1$,
o1, and o2 the number of O respectively bonded to M$^1$ and M$^2$,

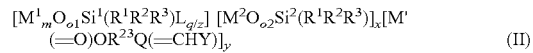

q/z is the number of counter anion L, $p+[o2\times(-2)]+1=0$,

R$^1$, R$^2$, and R$^3$ are each independent a substituent comprising 1 to 24 carbon atoms,
x ranges from 0 to 1000.

According to a second aspect, a solid organosilicon complex is described having Formula (II)

$$[M^1{}_mO_{o1}Si^1(R^1R^2R^3)L_{q/z}]\ [M^2O_{o2}Si^2(R^1R^2R^3)]_x[M'(\!\!=\!\!O)OR^{23}Q(\!\!=\!\!CHY)]_y \quad (II)$$

wherein
M$^1$ and M$^2$ are an element having an oxidation state of +p,
Si$^1$ is a Lewis acidic silicon connected to M$^1$ via an oxygen, wherein other atoms in the solid organosilicon compound are represented stoichiometrically in relation to Si$^1$,
q represents a charge for M$^1{}_mO_{o1}Si^1(R^1R^2R^3)$, wherein q ranges from 1 to 3,
L is a counter anion bounded to M$^1$ and has a negative charge of −z, wherein z ranges from 1 to 3,
Si$^2$ represents a silicon bounded to M$^2$ via an oxygen,
M' is a transition metal ion bounded to Si$^1$ via an oxygen,
m is a number of M$^1$,
o1, and o2 the number of O respectively bonded to M$^1$ and M$^2$,

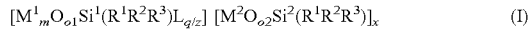

q/z is the number of counter anion L, $p+[o2\times(-2)]+1=0$,

R$^1$, R$^2$, and R$^3$ are each independent a substituent comprising 1 to 24 carbon atoms,
Q is NR$^{20}$R$^{21}$, or OR$^{22}$
wherein R$^{20}$, and R$^{21}$ are each independent a substituent comprising 1 to 10 carbon atoms or together constitute moiety having a 3 to 8 membered cyclic ring,
wherein R$^{22}$, and R$^{23}$ are each independent a substituent comprising 1 to 30 carbon atoms,
R$^{22}$, and R$^{23}$ are each independent a substituent comprising 1 to 30 carbon atoms,
Y is a substituent comprising 1 to 24 carbon atoms,
x ranges from 0 to 1000, and
0<y≤1.

According to a third aspect a catalytic system is described, for hydrodeflurorination (HDF) of a fluorocarbon compound, the catalytic system comprising the organosilicon compound of Formula (I), a fluorocarbon compound and a silane compound having at least one Si—H group.

According to a fourth aspect, a method to perform hydrodeflurorination (HDF) of a fluorocarbon compound is described. The method comprises contacting an organosilicon compound of Formula (I) with the fluorocarbon compound in presence of a silane compound having at least one Si—H group for a time and under condition to allow hydrodeflurorination of the fluorocarbon compound.

According to a fifth aspect, catalytic system for olefin homocoupling is described, the system comprising an organosilicon complex of Formula (II), and at least one terminal olefin monomer.

According to a sixth aspect, a method to perform olefin homocoupling is described, the method comprising contacting terminal olefin with an organosilicon complex of Formula (II), for a time and under condition to allow homocoupling of the terminal olefin.

According to a seventh aspect, catalytic system for olefin polymerization is described, the system comprising an organosilicon complex of Formula (II), and at least one acyclic diolefin monomer and/or the cyclic olefin monomer.

According to an eight aspect, a catalytic system for olefin polymerization is described, the system comprising an organosilicon complex of Formula (II), and at least one acyclic diolefin monomer and/or the cyclic olefin monomer.

According to a ninth aspect, a method is described for preparing a polyolefin polymer, the method comprising contacting at least one acyclic diolefin monomer and/or the cyclic olefin monomer with an organosilicon complex of Formula (II), for a time and under condition to allow polymerization of the at least one olefin monomer.

According to a tenth aspect, a method is described for preparing an organosilicon complex of Formula (II), the method comprises contacting an organosilicon compound Formula (I) with an organometallic compound of formula $$M'(=O)OR^{23}Q \ (=CHY) \quad (III)$$

wherein

Y is a substituent comprising 1 to 24 carbon atoms,

M' is a transition metal ion bounded to $Si^1$ via an oxygen, and

Q is $NR^{20}R^{21}$, or $OR^{22}$ in which $R^{20}$, and $R^{21}$ are each independent a substituent comprising 1 to 10 carbon atoms or together constitute moiety having a 3 to 8 membered cyclic ring, and $R^{22}$, and $R^{23}$ are each independent a substituent comprising 1 to 30 carbon atoms, and the contacting performed for a time and under condition to form the organosilicon complex Formula (II).

According to an eleventh aspect, a method is described for preparing an organosilicon compound of Formula (I), the method comprises contacting a solid oxide of Formula (IV)

$$[M^1{}_m HO_{o1} L_{q/z}][M^2 HO_{o2}]_x \quad (IV)$$

with a silane of Formula (V)

$$SiR^1 R^2 R^3 R^4 \quad (V)$$

wherein $M^1$ and $M^2$ are an element having an oxidation state of +p,

L is a counter anion bounded to $M^1$ and has a negative charge of −z, m is number of $M^1$, o1, and o2 the number of O respectively bonded to $M^1$ and $M^2$, $$(m \times p) + [o1 \times (-2)] + 1 = q,$$

q/z is the number of counter anion L, $$p + [o2'(-2)] + 1 = 0,$$

$R^1$, $R^2$, $R^3$, and $R^4$ are each independent a substituent comprising 1 to 24 carbon atoms, linear C1-C15 alkyl; branched C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group, an isopropyl, an allyl group, a chloride, a bromide, an iodide, or a triflate, and x ranges from 0 to 1000, the contacting performed for a time and under condition to form the organosilicon compound Formula (I).

The organosilicon on metal oxides and related compositions, methods and systems, can be used in several embodiments to selectively catalyze the breaking of C—F in the fluorocarbon compounds. In particular, the catalyst in the present disclosure can selectively catalyze breaking a sp3 C—F in the presence of a sp2 C—F bond. The catalyst of Formula (I) can also selectively catalyze breaking a sp3 C—F in the presence of a sp3 C—Cl, sp3 C—Br or sp3-I bonds as will be understood by a skilled person.

The organosilicon on metal oxides complexes and related compositions, methods and systems, can be used in several embodiments to perform olefin metathesis reaction and in particular to perform olefin homocoupling and olefin polymerization as will be understood by a skilled person.

The organosilicon on metal oxides and related complexes, compositions, methods and systems herein described can be used in connection with applications wherein fluorocarbon or olefin based reactions, and in particular olefin oligomerization and/or olefin polymerization in particular polymerization in the presence of polar additives or copolymerization of functionalized and non-functionalized monomers are desired. The polymerization of non-olefinic monomers is proposed as well. Exemplary applications comprise decontamination of fluorocarbon in the environment, synthesis of specialty chemicals, or any selective organic transformation to convert sp3 C—F bond to a sp3 C—H bond.

The details of one or more embodiments of the disclosure are set forth in the accompanying drawings and the description below. Other features and objects will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 5 panel b) shows $^{29}$Si Cross Polarization Magic Angle Spinning (CPMAS) spectrum of the organosilicon functionalized SZO 1 resulting from the reaction scheme in FIG. 5 Panel a.

FIG. 7A shows a $^{13}$-C CP-MAS NMR spectrum, spinning@8 kHz, 20 k scans; the chemical shifts for —CH— and -Me carbons in organosilicon functionalized SZO of Formula 1 are at 15 pm and 18 ppm respectively as illustrated. FIG. 7B shows $^1$H NMR spectrum of organosilicon functionalized SZO 1, spinning@8 kHz, 128 scans.

FIG. 11A shows the reaction scheme of allyltriisopropylsilane+Al$_2$O$_3$ to produce triisopropylsilane functionalized alumina $^i$Pr$_3$Si—Al$_2$O$_3$ (2) in C$_6$D$_6$ for 24 hours at room temperature.

FIG. 11B top panel shows the FTIR spectrum of the triisopropylsilane functionalized alumina $^i$Pr$_3$Si—Al$_2$O$_3$ (2) of FIG. 11A; FIG. 11B bottom panel shows FTIR spectrum of alumina (Al$_2$O$_3$) starting material.

FIG. 14 shows Table 1 reporting the values of $^{31}$P NMR chemical shifts of a TEPO (triethylphosphine oxide) complex of the present disclosure (Compound 1$^a$), together with corresponding $^{31}$P NMR chemical shifts values for selected silicon Lewis acids for comparison (Si(cat$^F$)$_2$$^b$, Si(Cat$^{Cl}$)$_2$$^b$, [Et$_3$Si]$^c$).

DETAILED DESCRIPTION

Figure 1A:
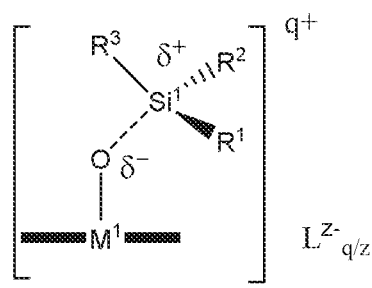
FIG. 1A shows a representation of a structure of Formula (VI) having an electrophilic organosilicon of partial positive charge δ−; in the illustration of FIG. 1A the structure has an electron deficient organosilicon oxide site supported on a solid metal oxide in ionic bonding contact with q/z number of counter anion L bearing a negative charge z to maintain charge neutrality of the structure as herein described.

Described herein are organosilicon on solid oxides and related complexes, compositions, methods and systems, which in several embodiments allow selective catalysis of organic chemical transformations.

The wording "solid organosilicon compound" as used herein indicates a silicon containing material in which the silicon forms at least one carbon-silicon bond with an organic moiety and a Si—O bond with the oxygen of an oxide in the solid state at room temperature.

The term "oxide" as used herein indicates a chemical compound that consists of at least one oxygen atom and one other element in its chemical formula. In particular, are dianion of oxygen, an $O^{2-}$ atom with either a metal element or a non-metal element. Exemplary metal elements that can be used in an oxide in accordance with the present disclosure include Al, Be, Bi, Cd, Co, Cr, Cu, Fe, Ca, La, Mn, Mo, Ni, Sn, Sr, Th, Ti, V, W, Y, Zn, Zr, and any combinations thereof. Exemplary non-metallic elements that can be used in an oxide in accordance with the present disclosures include B, Si, S, P, Sb.

In organosilicon compound oxides herein described, the electrophilic properties of the Si atom are key to the reactivity of the organosilicon compound and therefore the ability of the organosilicon compound to act a catalyst and to bind to nucleophiles as will be understood by a skilled person. Such electrochemical properties can be either calculated in terms of partial charge δ of the Si in the organosilicon compound or can be measured as chemical shift of phosphorus following binding with the Si of organosilicon compounds herein described.

The term "partial charge δ" of an atom or a group of atoms indicates a fractional electronic charge value measured in elementary charge units created due to a redistribution of the valence electron density in chemical bonds. The partial charge can be derived directly from experimental quantities, e.g., dipole moments, electrostatic potentials, or free energy differences. Alternatively, the partial charge can be calculated from quantum chemical calculations. The silicon atom of the organosilicon compound as disclosed herein has a partial charge δ of positive value that is less than 1 as denoted by $δ^+$ as shown, for example, in Formula (VI) of FIG. 1A.

In embodiments, herein described partial charges δ are calculated on silicon atom of the organosilicon compound. In some embodiments, the partial charge can be derived from a least-squares fit to the electrostatic potential calculated in a large number of points around the molecule of interest. Examples of such potential-based methods are charges from electrostatic potential ("CHELP") and charges from electrostatic potentials using a grid-based method ("CHELPG"). In the CHELP method, points are selected symmetrically on spherical shells around each atom (L. E. Chirlain and M. M. Francl, *J. Comput. Chem.*, 6, 894, 1987) while in the CHELPG method, points are selected on a regularly spaced cubic grid with increased point density (C. M. Breneman and K. B. Wiberg, *J. Comput. Chem.*, 11, 361, 1990).

In embodiments herein described, the partial charge δ of an atom or a united atom can be calculated as a CHELPG charge, (charges from electrostatic potentials using a grid-based method). In addition or in the alternative the partial charge can be calculated with quantum chemistry software such as Gaussian, GAMESS, and others identifiable to a person of ordinary skill in the art. Methods for calculating the partial charges are well documented in related literature and will be known to a person of ordinary skill in the art (R. S. Mulliken, *J. Chem. Phys.*, 23, 10, 1833-1840, 1955; F. L. Hirshfeld, Theor. Chem. Acc., 44, 129-38, 1977; U. C. Singh and P. A. Kollman, *J. Comp. Chem.*, 5, 129-45, 1984; A. E. Reed, R. B. Weinstock, and F. Weinhold, *J. Chem. Phys.*, 83, 2, 735-746, 1985; A. V. Marenich, S. V. Jerome, C. J. Cramer and D. G. Truhlar, *J. Chem. Theory Comput.*, 8, 527, 2012; L. E. Chirlain and M. M. Francl, *J. Comput. Chem.*, 6, 894, 1987; C. M. Breneman and K. B. Wiberg, *J. Comput. Chem.*, 11, 361, 1990). For example, in some instances, the electrostatic potential and CHELPG charges can be calculated with the quantum chemistry software Gaussian 94 using the hybrid density functional method B3LYP. In some other cases, the calculations can be performed with the ab initio Hartree-Fock (HF) method and with Moller-Plesset second-order perturbation theory (MP2).

The term "quantum chemical" or "quantum mechanics" calculations refer to calculation methods based on a number of classes of quantum chemical models that describe molecules in terms of interactions among nucleic and electrons and molecular geometry in terms of minimum energy arrangements of nuclei. Various levels of approximations have been developed to make a compromise between accuracy and computational cost. Exemplary approximation methods include Hartree-Fock approximation, Moller-Plesset model (MP), the second-order Moller-Plesset model (MP2), density functional theory (DFT), semi-empirical models that introduce empirical parameters to simplify the calculations, and other approximation models as will be recognized by a person skilled in the art of computational chemistry.

Density functional theory ("DFT") is an electron-density-based approximation method in which instead of solving the full Schrödinger equation for the many-electron wavefunction, two-particle probability density, i.e. the probability of finding an electron at position $r_1$ and an electron at position $r_2$, is employed for the purpose of calculating the ground state energy. Detailed description of density functional theory can be found in related literatures such as S. Grimme, J. Antony, S. Ehrlich, and H. Krieg, *J. Chem. Phys.*, 132, 154104, 2010; F. Weigend and R. Ahlrichs, *Phys. Chem. Chem. Phys.*, 7, 3297-3305, 2005.; J. Zheng, X. Xu, and D. Truhlar, *Theor. Chem. Acc.*, 128, 295-305, 2011; and C. M. Breneman and K. B. Wiberg, *J. Comp. Chem.*, 11, 361-373, 1990. herein incorporated by reference in its entirety.

Various approximations can be employed to replace the exact exchange energy resulting from the quantum nature of electrons with an exchange-correlation functional. Hybrid functionals are a class of approximation to the exchange-correlation function in density functional theory. The hybrid functionals incorporate a portion of exact exchange from Hartree-Fock theory with a portion of exchange and correlation from other sources. The exact exchange energy functional is expressed in terms of Kohn-Sham orbitals rather than density. One of the exchange-correlation functionals used in DFT is B3LYP (Becke, three-parameter, Lee-Yang-Parr). Another commonly known exchange-correlation functional is PBE functional that mixes PBE (Perdew-Burke-Ernzerhof) exchange and correlation energy with Hartree-Fock exchange energy. Many other hybrid functionals or non-hybrid functionals such as gradient-corrected methods including PBE can also be used in the current disclosure and are identifiable to a person skilled in the art. Detailed information about how to select approximate functional in the DFT methods can be found in related literatures as well as simulation package use manual such as the one available on the website gaussian.com/dft/ at the time of filing of the present application.

The partial charge of the silicon of the organosilicon as disclosed herein can also be experimentally determined based on the phosphorus-31 ($^{31}P$) nuclear magnetic resonance spectroscopy of the corresponding triethylphosphine oxide (TEPO or OPEt$_3$) adduct with the silicon atom as will be understood by a skilled person.

In embodiments herein described, the solid organosilicon compound has Formula (I)

$$[M^1{}_m O_{o1} Si^1(R^1R^2R^3)L_{q/z}] [M^2 O_{o2} Si^2(R^1R^2R^3)]_x \qquad (I)$$

wherein $M^1$ and $M^2$ are an element having an oxidation state of +p, wherein p ranges from 2 to 5, $Si^1$ is a Lewis acidic silicon connected to $M^1$ via an oxygen, wherein other atoms in the solid organosilicon compound are represented stoichiometrically in relation to $Si^1$, q represents a charge for $M^1{}_m O_{o1} Si^1(R^1R^2R^3)$, wherein q ranges from 1 to 3, L is a counter anion bounded to $M^1$ and has a negative charge of –z wherein z ranges from 1 to 3, $Si^2$ represents a silicon bounded to $M^2$ via an oxygen, m is number of $M^1$, o1, and o2 the number of O respectively bonded to $M^1$ and $M^2$, $$(m \times p) + [o1 \times (-2)] + 1 = q,$$

q/z is the number of counter anion L, $$p + [o2 \times (-2)] + 1 = 0,$$

$R^1$, $R^2$, and $R^3$ are each independent a substituent comprising 1 to 24 carbon atoms, such linear or branched substituted or unsubstituted aliphatic moiety (e.g. alkanyl, alkenyl, alkynyl, groups) cyclic moiety (e.g. aromatic or aliphatic moieties), x ranges from 0 to 1000.

In organosilicon compounds of Formula (I), $M^1$ and $M^2$ both refers to any element M on the periodic table that is capable of being in a solid oxide form at room temperature. The element of M can be any suitable main group metal elements like aluminum, a transition metal element like zirconium or a non-metallic element like boron.

In organosilicon compounds of Formula (I), one in m number atoms of $M^1$, which is on the surface of the oxide, is associated with counter anion L such that $M^1$ is capable of rendering $Si^1$ Lewis acidic through a bridging oxygen atom as shown in FIG. 1A. Accordingly, selection of a suitable pair of counter anion L and $M^1$ in Formula (I) can be performed to obtain a partial charge $\delta^+$ on $Si^1$ as shown FIG. 1A as will be understood by a skilled person.

In organosilicon compounds of Formula (I), the moiety of $M^1{}_m O_{o1} Si^1(R^1R^2R^3)$ possesses a net positive charge q which ranges from 1 to 3, which is charge balanced by the corresponding amount of counterion L which has a negative charge of –z.

In organosilicon compounds of Formula (I), only one in m number atoms of $M^1$ is bridged to $Si^1$. Accordingly, a higher density of catalytic centers of $Si^1$ can be achieved by lowering the number of m for $M^1$, for example by providing a higher surface area of solid oxide element M as will be understood by a skilled person.

Figure 1B:
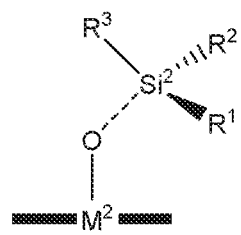
FIG. 1B shows a representation of a structure of Formula (VII) having a neutral organosilicon; in the illustration of FIG. 1B the structure has a substantially neutral organosilicon oxide site supported on a neutral solid metal oxide.
Figure 2:
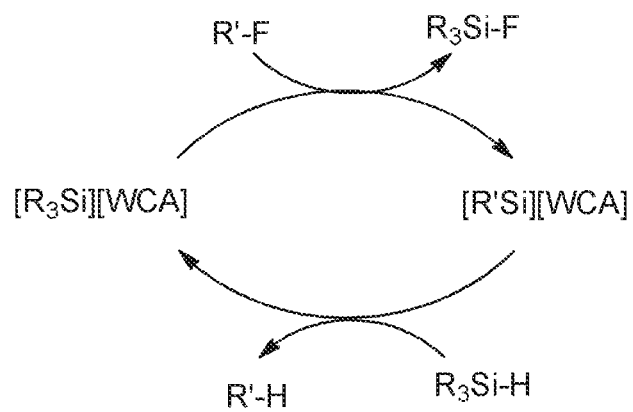
FIG. 2 shows a scheme of catalytic hydrodefluorination of a C—F bond with asylylium cation having a weakly coordinating anion (WCA), [R3 Si][WCA].
Figure 3:
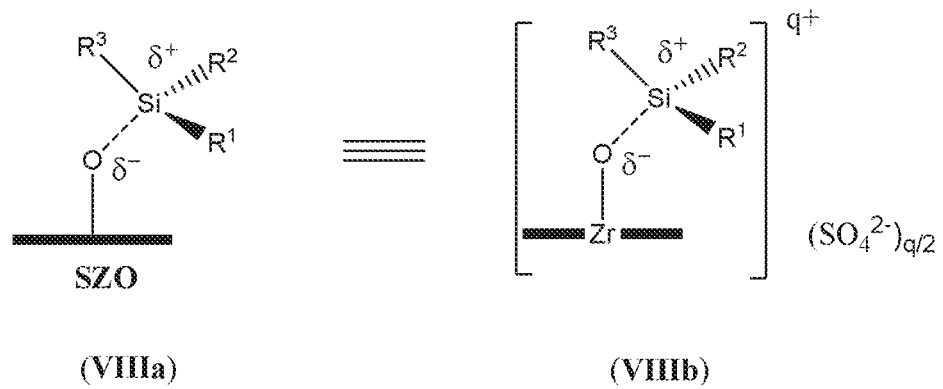
FIG. 3 shows the structure of an exemplary electrophilic organosilicon of the disclosure having partial positive charge δ+; in the illustration of FIG. 3, the structure has an electron deficient organosilicon oxide site supported a sulfated zirconium oxide (SZO) in which the Formula (VIIIa) and Formula (VIIIb) represent the equivalent structures.
Figure 4:
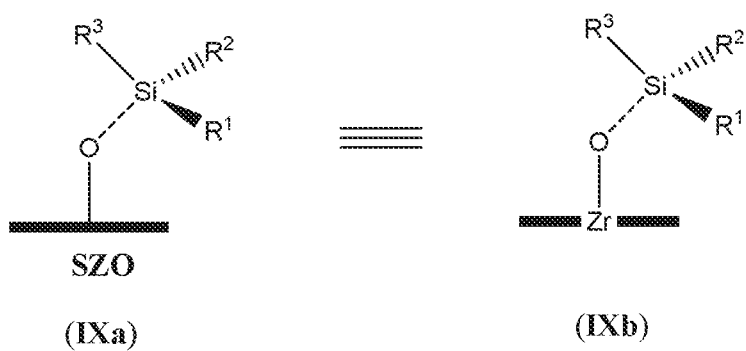
FIG. 4 shows a representation of a structure of an exemplary neutral organosilicon of the present disclosure; in the illustration of FIG. 4 the structure has a substantially neutral organosilicon oxide site supported on a zirconium oxide (ZO) which is not sulfated coexisting with sulfated zirconium oxide (SZO) in which the Formula (IXa) and Formula (IXb) represent the equivalent structures.

In organosilicon compounds of Formula (I), an atom of $M^2$ is typically at least two atoms spaced apart from counter anion L such that $M^2$ is incapable of rendering $Si^2$ Lewis acidic through a bridging oxygen atom as shown in FIG. 1B. Accordingly, typically a suitable pair of counter anion L and $M^2$ in organosilicon compound of Formula (I) is unable to create a substantial partial charge $\delta^+$ on $Si^2$ as shown FIG. 1B.

In organosilicon compounds of Formula (I) herein described, the moiety of $M^2 O_{o2} Si^2(R^1R^2R^3)$ is charge neutral.

In embodiments herein described, $Si^1$ in Formula (I) refers to an electrophilic silicon. FIG. 1A illustrates the structure of the electrophilic $Si^1$ atom bridged to $M^1$ via an oxygen atom in association with a counter anion in the moiety $[M^1{}_m O_{o1} Si^1(R^1R^2R^3)L_{q/z}]$ for Formula (I).

In particular, FIG. 1A shows a representation of a structure of the moiety $[M^1{}_m O_{o1} Si^1(R^1R^2R^3)L_{q/z}]$ having an electrophilic organosilicon of partial positive charge $\delta^+$, the structure has an electron deficient organosilicon oxide site supported on a solid metal oxide in ionic bonding contact with q/z number of counter anion L bearing a negative charge z to maintain charge neutrality of the structure as herein described.

In contrast $Si^2$ refers to a substantially neutral silicon in Formula (I). FIG. 1B illustrates the structure of a substantially neutral $Si^2$ atom bridged to $M^2$ via an oxygen atom that is not in association with a counter anion. As used herein, the term substantially neutral refers to charge neutrality of an atom that has a partial charge in the range of −0.05 to +0.05. In some embodiments, as herein described, a substantially neutral silicon has, when complexed to triethylphosphine oxide, a change in chemical shift (Δδ) of triethylphosphine oxide in $^{31}P\{1H\}$ MAS NMR spectrum not more than 10 ppm shift downfield (larger ppm) compared to physisorbed O=PEt3, 50 ppm in the solid state (Osegovic, J. P.; Drago, R. S. J. Catal. 1999, 182, 1-4).

In organosilicon compounds of Formula (I), $Si^2$ is typically spaced at least two atoms apart from L.

In organosilicon compounds of Formula (I), the molar ratio of neutral $Si^2$ to the associated oxide element $M^2$ is 1. In contrast the remaining element M of Formula (I) are defined as $M^1$. Therefore, $M^1$ include the element M in the bulk or interior of the solid oxide of M as well as the element M that are bound to $Si^1$ via oxygen.

In organosilicon compounds of Formula (I), m is the molar ratio of $M^1$ relative to $Si^1$ in Formula (I). As disclosed herein, o1, and o2 in Formula (I) are the number of O respectively bonded to $M^1$ and $M^2$. As disclosed herein, p refers to the charge of element M in Formula 1.

In some embodiment of solid organosilicon compound as described herein, m of Formula (I) refers to the molar ratio of element $M^1$, which is element M of the oxide that is not bound to any neutral silicon $Si^2$ via an oxygen, relative to the electrophilic silicon atom $Si^1$.

In maintaining the charge neutral for the solid organosilicon compound of Formula (I), the conditions of the following equations are met $(m \times p)+[o1\times(-2)]+1=q$, and $p+[o2\times(-2)]+1=0$.

In organosilicon compounds of Formula (I), q/z is the number of counter anion L, which ensures the charge neutrality of the electrophilic silicon and the associated elements $M^1$ and oxygen of o1.

In some embodiments of compounds of Formula (I), M of $M^1$ and $M^2$ of Formula (I) can be selected from the group consisting of Al, B, Be, Bi, Cd, Co, Cr, Cu, Fe, Ca, La, Mn, Mo, Ni, Sn, Sr, Th, Ti, V, W, Y, Zn, Zr, Si, P, S, Sb and any combinations thereof. Preferably, wherein M1 and M2 are selected from the group consisting of Al, Zn, and Zr, and any combinations thereof. Particularly, $M^1$ and $M^2$ can be Zr.

In some embodiments of compounds of Formula (I), p can be 2, 3 4 or 5.

In some embodiment of solid organosilicon compound as described herein, L of Formula (I) can be selected from the group consisting of sulfate ($SO_4^{2-}$), sulfite ($SO_3^{2-}$), selenate ($SeO_4^{2-}$), phosphate ($PO_4^{3-}$), phosphate ($PO_4^{3-}$), pyrophosphate ($P_2O_7^{4-}$), chloride ($Cl^-$), chlorate ($ClO_3^-$), bromide ($Br^-$), bromate ($BrO_3^-$), tetraborate ($B_4O_7^{2-}$), vanadate ($VO_4^{3-}$), tungstate ($WO_4^{2-}$), molybdate ($MoO_4^{2-}$), p-toluene sulfonic acid, and any combinations thereof.

In organosilicon compound of Formula (I) the CHELPG charge of the silicon atom $Si^1$ has a value greater than or equal to 0.1, preferably in a range between 0.25 and 0.75.

In organosilicon compound of Formula (I), the OPEt3 adduct of the organosilicon compound as described herein can have a change in chemical shift (Δδ) of triethylphosphine oxide in $^{31}P\{1H\}$ MAS NMR spectrum at least 15 ppm shift downfield (larger ppm) compared to physisorbed O=PEt3, 50 ppm in the solid state (Osegovic, J. P.; Drago, R. S. J. Catal. 1999, 182, 1-4).

In organosilicon compound of Formula (I), each one of $R^1$, $R^2$, and $R^3$ can be independently a linear C1-C15 alkyl; branched C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group.

In organosilicon compounds of Formula (I), the term x in of the solid organosilicon compound refers to the molar ratio of neutral silicon $Si^2$ to electrophilic silicon $Si^1$. In some embodiments, the molar ratio of neutral silicon $Si^2$ to electrophilic silicon $Si^1$ can range from 0 to 1000.

Therefore, in some embodiments, the solid organosilicon compound as described herein has Formula (Ia) when x for Formula (I) is 0

$$M^1{}_m O_{o1} Si^1(R^1R^2R^3)L_{q/z} \quad \text{(Ia)}$$

In some embodiments of the organosilicon compound of Formula (I), L can be a sulfate ($SO_4^{2-}$) and z is 2.

In some embodiments of the organosilicon compound herein described the solid organosilicon compound of claim 1, wherein x ranges from 0.05 to 10.

In some embodiments of the organosilicon compound of Formula (I), x ranges from 0.1 to 1

In some embodiments of the organosilicon compound of Formula (I), x ranges from 0.15 to 0.5.

In some embodiments of the organosilicon compound of Formula (I), x can be 0.25 (see Example 4).

In some embodiments of the organosilicon compound of Formula (I), m ranges from 10 to 1000, or from 20 to 100 or from 40 to 80.

In some embodiments of the organosilicon compound of Formula (I), $M^1$ and $M^2$ are Zr having an oxidation state of +4, $Si^1$ is a Lewis acidic silicon connected to $M^1$ via an oxygen, wherein other atoms in the solid organosilicon compound are represented in relation to $Si^1$, L is a sulfate anion bounded to $M^1$ and has a negative charge of −2, $Si^2$ represents a silicon bounded to $M^2$ via an oxygen and is at least two atoms spaced apart from the sulfate anion, m ranges from 10 to 1000, o1, and o2 the number of O respectively bonded to $M^1$ and $M^2$, $4m+[o1\times(-2)]+1=q$, q/2 is the number of the sulfate, o2=2.5, $R^1$, $R^2$, and $R^3$ are each independent a substituent comprising 1 to 24 carbon atoms, x ranges from 0.05 to 10.

In embodiments herein described an organosilicon compound of Formula (I) can be comprised in a catalytic system for hydrodefluorination (HDF) of a fluorocarbon compound, the system comprising one or more organosilicon compound of Formula (I), the fluorocarbon compound and a silane compound having Si—H.

In some embodiments of the catalytic system for hydrodefluorination (HDF) herein described, the fluorocarbon includes a sp³ C—F bond.

In some embodiments of the catalytic system for hydrodefluorination (HDF) herein described, the fluorocarbon is represented by Formula (XI)

$$C_nH_{2n+2-s}F_s \quad \text{(XI)}$$

wherein
n ranges from 1 to 30, and
s ranges from 1 to 2n.

In some embodiments of the catalytic system for hydrodefluorination (HDF) herein described, the fluorocarbon is benzotrifluoride, octofluorotoluene, or 1-fluoroadamatane (see Examples 5 to 7).

In some embodiments of the catalytic system for hydrodefluorination (HDF) herein described, the fluorocarbon is represented by Formula (XII)

wherein
R" is selected from the group consisting of a linear C1-C15 alkyl; branched C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group.

In some embodiments of the catalytic system for hydrodefluorination (HDF) herein described, the silane compound is selected from the group consisting of triethylsilane, diethylmethylhydrosilane, polymethylhydrosilane (PMHS), methyldiethoxysilane, diethoxydimethylsilane triethoxysilane.

In embodiments herein described one or more organosilicon compound of Formula (I) can be used in a method to perform hydrodefluorination (HDF) of a fluorocarbon compound is described. The method comprises contacting an organosilicon compound of Formula (I) with the fluorocarbon compound in presence of a silane compound comprising at least one Si—H group for a time and under condition to allow hydrodefluorination of the fluorocarbon compound.

In some embodiments, method for hydrodefluorination (HDF) of a fluorocarbon compound can be carried out under conditions at a temperature between 0° C. and 150° C., in an alkane or aromatic solvent, at concentrations ranging from ~0.01-10M in fluorocarbon compound. The fluorocarbon can be contacted in the gas phase or solution phase, in the presence or the absence of the silane, and can be contacted "neat" (without solvent). The reaction is initiated when the silane is added to the mixture.

In some embodiments, the organosilicon compound of Formula (I) can form a solid organosilicon complex having Formula (II)

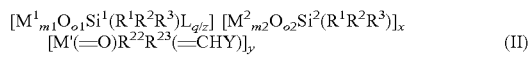

wherein
wherein
$M^1$ and $M^2$ are an element having an oxidation state of +p,
$Si^1$ is a Lewis acidic silicon connected to $M^1$ via an oxygen, wherein other atoms in the solid organosilicon compound are represented stoichiometrically in relation to $Si^1$,
q represents a charge for $M^1{}_mO_{o1}Si^1(R^1R^2R^3)$, wherein q ranges from 1 to 3,
L is a counter anion bounded to $M^1$ and has a negative charge of $-z$, wherein z ranges from 1 to 3,
$Si^2$ represents a silicon bounded to $M^2$ via an oxygen and is at least two atoms spaced apart from L,
M' is a transition metal ion bounded to $Si^1$ via an oxygen, m is a number of $M^1$,
o1, and o2 are the number of O respectively bonded to $M^1$ and $M^2$, wherein $(m \times p)+[o1 \times (-2)]+1=q$, q/z is the number of counter anion L, $p+[o2 \times (-2)]+1=0$, $R^1$, $R^2$, and $R^3$ are each independent a substituent comprising 1 to 24 carbon atoms, Q is $NR^{20}R^{21}$, or $OR^{22}$
wherein $R^{20}$, and $R^{21}$ are each independently a substituent comprising 1 to 10 carbon atoms such linear or branched substituted or unsubstituted aliphatic moiety (e.g. alkanely, alkenyl alkynyl, groups) cyclic moiety (e.g. aromatic or aliphatic moieties)
wherein $R^{22}$, and $R^{23}$ are each independently a substituent comprising 1 to 30 carbon atoms such linear or branched substituted or unsubstituted aliphatic moiety (e.g. alkanely, alkenyl alkynyl, groups) cyclic moiety (e.g. aromatic or aliphatic moieties),
Y is a substituent comprising 1 to 24 carbon atoms,
x ranges from 0 to 1000, and
y ranges from 0 to 1.

In some embodiments, in solid organosilicon complex of Formula (II), $M^1$ and $M^2$ are selected from the group consisting of Al, Be, Bi, Cd, Co, Cr, Cu, Fe, Ca, La, Mn, Mo, Ni, Sn, Sr, Th, Ti, V, W, Y, Zn, Zr, B, Si, S, P, Sb and any combination thereof.

In some embodiments, in solid organosilicon complex of Formula (II), $M^1$ and $M^2$ are selected from the group consisting of Al, Zn, and Zr, and any combination thereof.

In some embodiments, in solid organosilicon complex of Formula (II), $M^1$ and $M^2$ are Zr.

In some embodiments, in solid organosilicon complex of Formula (II), L is selected from the group consisting of sulfate ($SO_4{}^{2-}$), sulfite ($SO_3{}^{2-}$), selenate ($SeO_4{}^{2-}$), phosphate ($PO_4{}^{3-}$), phosphate ($PO_4{}^{3-}$), pyrophosphate ($P_2O_7{}^{4-}$), chloride ($Cl^-$), chlorate ($ClO_3{}^-$), bromide ($Br^-$), bromate ($BrO_3{}^-$), tetraborate ($B_4O_7{}^{2-}$), vanadate ($VO_4{}^{3-}$), tungstate ($WO_4{}^{2-}$), molybdate ($MoO_4{}^{2-}$), p-toluene sulfonate, trifluoroacetate and any combination thereof.

In some embodiments, in solid organosilicon complex of Formula (II), L is sulfate ($SO_4{}^{2-}$) and z is 2.

In some embodiments, in solid organosilicon complex of Formula (II), wherein x ranges from 0.05 to 10, or from 0.1 to 1, or from 0.15 to 0.5.

In some embodiments, in solid organosilicon complex of Formula (II), m ranges from 10 to 1000, or from 20 to 100, or from 40 to 80.

In some embodiments, in solid organosilicon complex of Formula (II), $M^1$ and $M^2$ are Zr having an oxidation state of +4, $Si^1$ is a Lewis acidic silicon connected to $M^1$ via an oxygen, wherein other atoms in the solid organosilicon compound are represented in relation to $Si^1$, L is a sulfate anion bounded to $M^1$ and has a negative charge of $-2$, $Si^2$ represents a silicon bounded to $M^2$ via an oxygen and is at least two atoms spaced apart from the sulfate anion, m ranges from 10 to 1000, o1, and o2 the number of O respectively bonded to $M^1$ and $M^2$, $4m+[o1\times(-2)]+1=q$, q/2 is the number of the sulfate, o2=2.5, $R^1$, $R^2$, and $R^3$ are each independent a substituent comprising 1 to 24 carbon atoms, x ranges from 0.05 to 10.

In some embodiments, in solid organosilicon complex of Formula (II), M' is Mo.

In some embodiments, of solid organosilicon complex of Formula (II), $R^{20}$, and $R^{21}$ can each independently be a linear C1-C15 alkyl; branched C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group. In the alternative, $R^{20}$ and $R^{21}$ together constitute moiety having a 3 to 8 membered cyclic ring containing the nitrogen to which $R^{20}$ and $R^{21}$ are bonded.

In some embodiments, of solid organosilicon complex of Formula (II),$R^{22}$, and $R^{23}$ can each independently be a linear C1-C15 alkyl; branched C3-C15 alkyl; cyclic C3-C15 alkyl;

linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group.

In some embodiments, in solid organosilicon complex of Formula (II), R22 is selected from the group consisting of H, linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl In some embodiments, in solid organosilicon complex of Formula (II), R23 is selected from the group consisting of linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl, group.

In some embodiments, in solid organosilicon complex of Formula (II), Y is selected from the group consisting of linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group.

In some embodiments, in solid organosilicon complex of Formula (II), y is at least 0.1.

In some embodiments, in solid organosilicon complex of Formula (II), R22 is selected from the group consisting of H, linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl, In some embodiments, in solid organosilicon complex of Formula (II), R23 is 2,6-bis(2,4,6-trimethylphenyl)phenyl or 2,6-bis(2,5-diphenyl-1H-pyrrol-1-yl)phenyl group.

In some embodiments, in solid organosilicon complex of Formula (II), Y is a 4-methoxyphenyl group.

In some embodiments the organosilicon complex of Formula (II) herein described can be included in a catalytic system for olefin homocoupling, the system comprising an organosilicon complex of Formula (II), and a terminal olefin monomer.

In some embodiments of the catalytic system for olefin homocoupling of the present disclosure, the at least one terminal olefin monomer is represented by Formula (XIII)

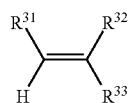

(XIII)

wherein
R$^{31}$ is H, methyl or ethyl group,
R$^{32}$ is H, linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group.

In some embodiments of the catalytic system for olefin homocoupling of the present disclosure, R$^{31}$ and R$^{32}$ in Formula (XIII) are H.

In some embodiments of the catalytic system for olefin homocoupling of the present disclosure, the at least one terminal olefin monomer is 1-decene.

In embodiments herein described, an organosilicon complex of Formula (II) and/or any one of the catalytic system of the disclosure to perform olefin homocoupling, can be used in a method to perform olefin homocoupling, comprising contacting terminal olefin with an organosilicon complex of Formula (II), for a time and under condition to allow homocoupling of the terminal olefin.

In some embodiments, organosilicon complex of Formula (II) in accordance with the present disclosure, can be comprised in a catalytic system for olefin polymerization, the system further comprising and at least one terminal diolefin monomer and/or a cyclic olefin monomer.

In some embodiments of the catalytic systems for olefin polymerization of the present disclosure, the terminal diolefin monomer is represented by Formula (XIV)

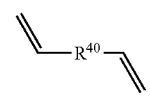

(XIV)

wherein
R$^{40}$ is a linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group.

In some embodiments of the catalytic systems for olefin polymerization of the present disclosure, the terminal diolefin monomer is represented by Formula (XIVa)

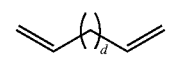

(XIVa)

wherein
d ranges from 1 to 20.

In some embodiments of the catalytic systems for olefin polymerization of the present disclosure, the cyclic olefin monomer is represented by Formula (XV)

(XV)

wherein R41 is a substituted or unsubstituted C1 to C10 alkylene group.

In some embodiments the organosilicon complex of Formula (II) or the catalytic systems for olefin polymerization of the present disclosure, can be used in a method for preparing polyolefin polymers, the method comprising contacting two or more olefin monomers with an organosilicon complex of Formula (II), for a time and under condition to allow polymerization of the two or more olefin monomers.

In accordance with the present disclosure, a method is described for preparing an organosilicon compound of Formula (I), the method comprises contacting a solid oxide of Formula (IV)

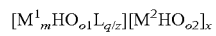

(IV)

with a silane of Formula (V)

wherein
- $M^1$ and $M^2$ are an element having an oxidation state of +p,
- L is a counter anion bounded to $M^1$ and has a negative charge of –z,
- m is number of $M^1$,
- o1, and o2 the number of O respectively bonded to $M^1$ and $M^2$, $$(m\times p)+[o1\times(-2)]+1=q,$$

q/z is the number of counter anion L, $$p+[o2\times(-2)]+1=0,$$

- $R^1$, $R^2$, $R^3$, and $R^4$ are each independent a substituent comprising 1 to 24 carbon atoms, such as a linear or branched substituted or unsubstituted aliphatic moiety (e.g. alkanyl, alkenyl, alkynyl groups) a cyclic moiety (e.g. aromatic or aliphatic moieties) a chloride, a bromide, an iodide, or a triflate,
- x ranges from 0 to 1000, the contacting performed for a time and under condition to form the organosilicon compound Formula (I).

In some embodiments of the method is described for preparing an organosilicon compound of Formula (I), $M^1$ and $M^2$ are Mo having an oxidation state of +4, L is a sulfate anion bounded to $M^1$ and has a negative charge of –2, and/or $R^2$, and $R^3$ are each isopropyl group.

In some embodiments of the silane of Formula (V) wherein $R^2$, $R^3$, and $R^4$ independently are a substituent comprising 1 to 24 carbon atoms, each of $R^1$, $R^2$, $R^3$, and $R^4$ can independently be a linear C1-C15 alkyl; a branched C3-C15 alkyl; a cyclic C3-C15 alkyl; a linear, cyclic, or branched C2-C15 alkenyl; a linear, cyclic, or branched C2-C15 alkynyl; a C6-C20 substituted or unsubstituted aryl; and C6-C20 substituted or unsubstituted heteroaryl group, an isopropyl, and/or an allyl group.

In accordance with the present disclosure, a method is described for preparing an organosilicon complex of Formula (II), the method comprises contacting an organosilicon compound Formula (I) with an organometallic compound of formula

wherein
- M' is a transition metal ion bounded to $Si^1$ via an oxygen,
- Y is a substituent comprising 1 to 24 carbon atoms and
- Q is $NR^{20}R^{21}$, or $OR^{22}$,
  in which
  - $R^{20}$, and $R^{21}$ are each independently a substituent comprising 1 to 10 carbon atoms, such as a linear or branched substituted or unsubstituted aliphatic moiety (e.g. alkanely, alkenyl alkynyl, groups) a cyclic moiety (e.g. aromatic or aliphatic moieties)
  , or together constitute moiety having a 3 to 8 membered cyclic ring, and
  - $R^{22}$, and $R^{23}$ are each independent a substituent comprising 1 to 30 carbon atoms, such as a linear or branched substituted or unsubstituted aliphatic moiety (e.g. alkanely, alkenyl alkynyl, groups) a cyclic moiety (e.g. aromatic or aliphatic moieties)

the contacting performed for a time and under condition to form the organosilicon complex Formula (II).

In some embodiments of the organometallic compound of Formula (III) $R^{20}$, and $R^{21}$ are each independently be a linear C1-C15 alkyl; branched C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group.

In some embodiments of the organometallic compound of Formula (III) $R^{22}$, and $R^{23}$ are each independently be a linear C1-C15 alkyl; branched C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group.

In some embodiments of the method is described for preparing an organosilicon complex of Formula (II), M' is Mo, Q is pyrrolide, 2,5-dimethylpyrrolide group, or $OR^{22}$ wherein $R^{22}$ is selected from the group consisting of linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl, 2,6-bis(2,4,6-trimethylphenyl)phenyl or 2,6-bis(2,5-diphenyl-1H-pyrrol -1-yl)phenyl group, $R^{23}$ is 2,6-bis(2,4,6-trimethylphenyl)phenyl or 2,6-bis(2,5-diphenyl-1H-pyrrol-1-yl)phenyl group, and/or Y is a 4-methoxyphenyl group.

As disclosed herein, 2,6-bis(2,4,6-trimethylphenyl)phenoxy group is represented by Formula ($IX_d$)

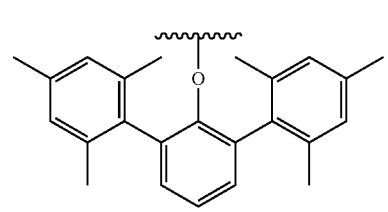

Formula ($IX_d$)

In some embodiments of the method is described for preparing an organosilicon complex of Formula (II), M' is Mo, Q is 2,6-bis(2,4,6-trimethylphenyl)phenoxy group, $R^{23}$ is 2,6-bis(2,4,6-trimethylphenyl)phenyl group, and/or Y is a 4-methoxyphenyl group.

Additional embodiments of the organosilicon compounds and related complexes methods and systems as well as further details concerning specific steps of the methods of the disclosure, related reaction conditions, concentrations, related products and general manufacturing of the of the organosilicon compounds and related complexes and systems inclusive of kit of parts, can be identified by the person skilled in the art upon reading of the present disclosure.

EXAMPLES

The following examples show exemplary organosilicon compounds 1 and 2 and exemplary organosilicon complex TIPSi-SZO$_{300}$-Mo1 as well as related exemplary methods and systems of making and using in catalytic reactions. A skilled person will be able to apply the guidance provided in the following examples for making and using additional organosilicon compounds and organosilicon complexes and related methods and system in accordance with the disclosure.

Accordingly, the following examples are provided for further illustration of embodiments of the present disclosure and are not intended to be limiting in any way.

General Conditions

All manipulations were performed under an inert atmosphere of nitrogen or argon using standard Schlenk or high vacuum techniques. (Duward F. Shriver, and M. A. Drezdzon, The Manipulation of Air-Sensitive Compounds, 2nd Edition, Wiley-Interscience, 1986, 336 pages).

Cyclohexane-D12, and benzene-D6 were purchased from Cambridge Isotope laboratories. Benzene, pentane, and cyclohexane were dried over sodium/benzophenone, degassed and distilled under vacuum. Pentane for the grafting reactions was dried over tetraglyme/sodium/benzophenone, degassed and distilled under vacuum. Allyltriisopropylsilane were dried over 4 Å sieves. Triethylsilane, trifluorotoluene, octaflurotoluene, hexafluorobenzene, perflurohexane, hexamethyldisilazane (HMDS), and triethylamine were dried over $CaH_2$ then vacuum distilled just prior to use. Other commercially available reagents were used as received without any purification. Synthesis of SZO and 1-fluoroadamantane (dried by sublimation) have been reported previously. (Comas-Vives, A.; Valla, M.; Copéret, C.; Sautet, P. ACS Cent. Sci. 2015, 1, 313-319; Comas-Vives, A.; Schwarzwälder, M.; Copéret, C.; Sautet, P. J. Phys. Chem. C 2015, 119, 7156-7163; Valla, M.; Wischert, R.; Comas-Vives, A.; Conley, M. P.; Verel, R.; Copéret, C.; Sautet, P. J. Am. Chem. Soc. 2016, 138, 6774-6785; Wischert, R.; Copéret, C.; Delbecq, F.; Sautet, P. Angew. Chem. Int. Ed. 2011, 50, 3202-3205; Angew. Chem. 2011, 123, 3260-3263; Wischert, R.; Laurent, P.; Copéret, C.; Delbecq, F.; Sautet, P. J. Am. Chem. Soc. 2012, 134, 14430-14449. f) Wischert, R.; Coperet, C.; Delbecq, F.; Sautet, P. Chem. Comm. 2011, 47, 4890-4892; Ahrens, M.; Scholz, G.; Braun, T.; Kemnitz, E. Angew. Chem. Int. Ed. 2013, 52, 5328-5332; Angew. Chem. 2013, 125, 5346-5440; Kemnitz, E.; Gross, U.; Rudiger, S.; Shekar, C. S. Angew. Chem. Int. Ed. 2003, 42, 4251-4254; Angew. Chem. 2003, 115, 4383-4386; Krahl, T.; Kemnitz, E. Cat. Sci. Tech. 2017, 7, 773-796.)

Solution phase $^1H$ spectroscopy was carried out on an Avance Bruker 300 or an Avance Bruker NEO400 and the spectra were referenced to the NMR solvent residual peak. Solution phase $^{19}F\{^1H\}$ spectroscopy was carried out on an Avance Bruker 300 (282 MHz) and the spectra were referenced to an internal standard of $C_6F_6$. Solid state NMR spectra were recorded in 4 mm zirconia rotors at 8-12 KHz magic angle spinning on an Avance Bruker NEO600 [$^{13}$-C (151 MHz) and $^{31}P$ (243 MHz)]. FT-IR spectra were recorded as pressed pellets using a Bruker Alpha IR spectrometer in an argon-filled glovebox. Gas chromatography was carried out using Agilent 7820A GC system equipped with an Alumina/KCl column for gas phase measurements or on a HP-5 column for solution measurements. Elemental analyses were carried out in the Microanalysis Laboratory at the University of Illinois Urbana-Champaign.

Example 1

The Reaction of SZO with Allyltriisopropylsilane to Produce Exemplary Organosilicon Compound 1

To SZO (1 g, 0.13 mmol OH) in a rotofloe, pentane (5 ml) was transferred under high vacuum ($10^{-5}$ torr) to the flask at 77 K. The slurry was warmed to room temperature and allyltriisopropylsilane (0.16 mL, 0.7 mmol, 5 equiv.) was added by syringe under argon flow. The slurry was sealed and stirred at room temperature for 3 hours. The volatiles were transferred to a rotafloe under vacuum, and the yellow solid was washed by vacuum transferring in new pentane and removing it by cannula (3×5 ml). The solid was dried under high vacuum. Analysis of the volatiles by gas chromatography revealed 0.12(±0.01) mmol/g (92% of OH loading) of propene and 0.041(±0.003) mmol/g (31% of OH loading) of propane were made during the reaction.(Damien B. Culver Matthew P. Conley, Activation of C—F Bonds by Electrophilic Organosilicon Sites Supported on Sulfated Zirconia, Angewandte Chemie, International ed., 57 (45), 2018, 14902-14905).

Figure 5:
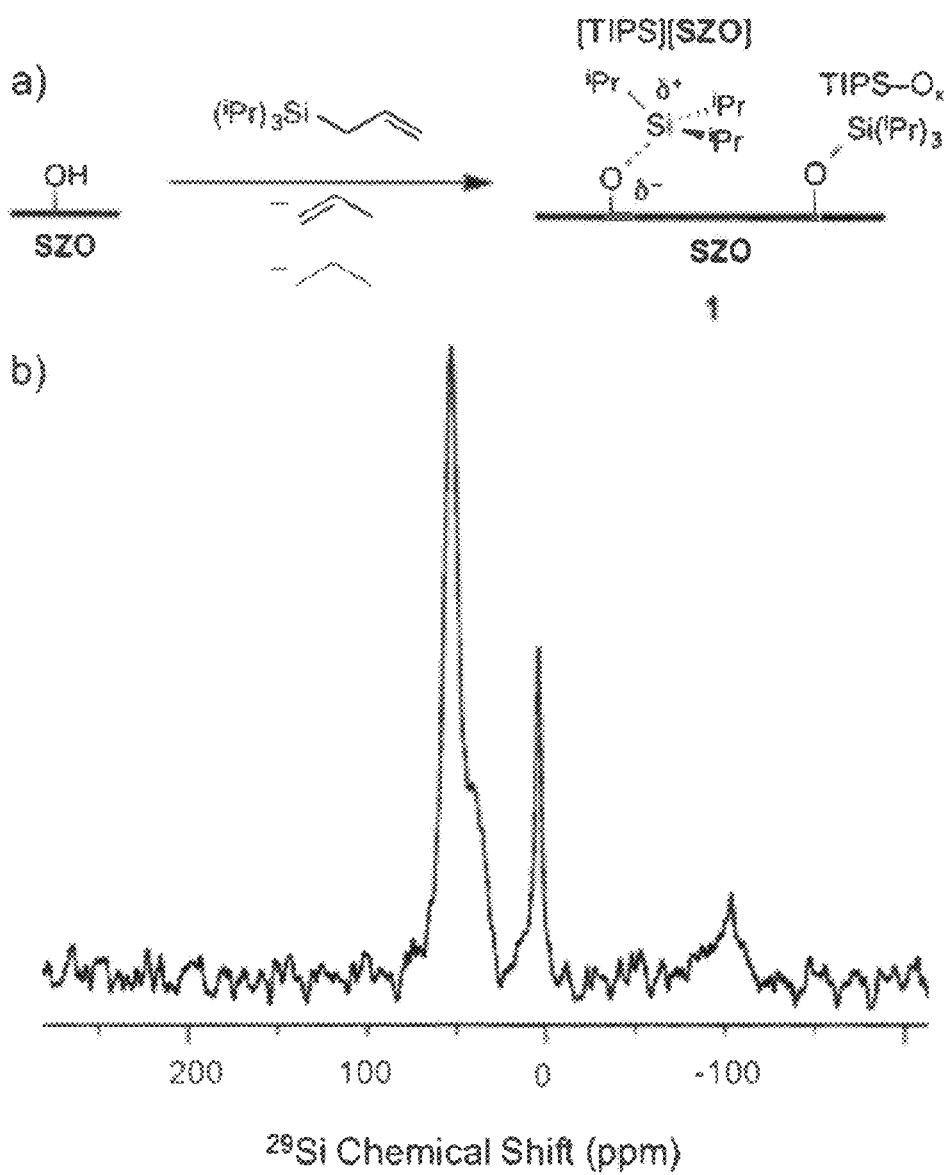
FIG. 5 panel a) illustrates a reaction scheme of partially dehydroxylated SZO with allyltriisopropylsilane in pentane slurry which results in the formation of organosilicon functionalized SZO 1.

The reaction of SZO dehydroxylated at 300° C. (0.13 mmol OH/g) with allyltriisopropylsilane in pentane slurry results in the formation of 1 (FIG. 5, panel a). This reaction generates 0.12 mmol/g propene, indicating that most of the acidic OH sites on $SZO_{300}$ react with the silane. This reaction also results in 0.041 mmol/g of propane, suggesting side reactions also occur. The $^{29}Si$ Cross Polarization Magic Angle Spinning (CPMAS) spectrum of 1 is shown in FIG. 5, panel b and contains signals at 53, 43, 4, and −100 ppm. The higher frequency signals are generally associated with more electron deficient trialkylsilyl groups, (Xie, Z.; Manning, J.; Reed, R. W.; Mathur, R.; Boyd, P. D. W.; Benesi, A.; Reed, C. A. J. Am. Chem. Soc. 1996, 118, 2922-2928) and support the formation of Lewis acidic silicon [TIPS][SZO] in 1. The signal at 4 ppm is consistent with the formation of TIPS-$O_x$, indicating that not all OH sites on SZO support the formation of Lewis acid sites. The $^{29}Si$ CPMAS signal at −100 ppm indicates that small amounts of $SiO_x$ species form in this reaction as will be understood by skilled person.

Example 2

Characterization of the Exemplary Organosilicon Compound 1

The characterization of the organosilicon compound 1 provided in Example 1 was performed by Gutmann-Beckett method. The Gutmann-Beckett method measures of the strength of a Lewis acid in solution (Mayer, U.; Gutmann, V.; Gerger, W. Monatsh. Chem. 1975, 106, 1235-1257; Beckett, M. A.; Brassington, D. S.; Coles, S. J.; Hursthouse, M. B. Inorg. Chem. Commun. 2000, 3, 530-533); or in solids (Osegovic, J. P.; Drago, R. S. J. Catal. 1999, 182, 1-4) by determining the change in chemical shift (Δδ) of triethylphosphine oxide (physisorbed O=PEt$_3$, 50 ppm in the solid state (Osegovic, J. P.; Drago, R. S. J. Catal. 1999, 182, 1-4)) when bound to the Lewis acid. Larger values of change in chemical shift (Δδ) indicate the stronger Lewis acids as will understood by a skilled person.

Figure 8A:
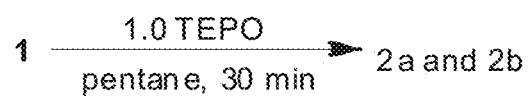
FIG. 8A shows a reaction scheme for the reaction of the organosilicon functionalized SZO of Formula 1 shown in FIG. 5 +TEPO (triethylphosphine oxide).
Figure 8B:
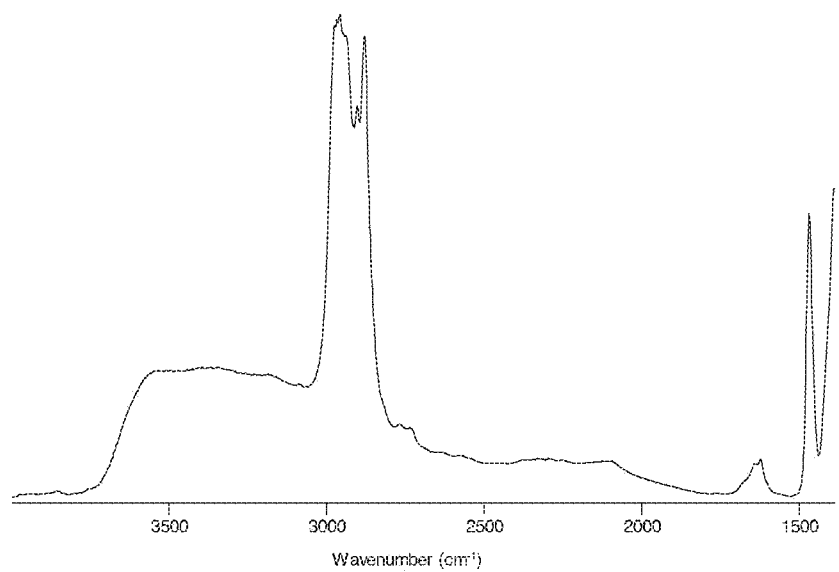
FIG. 8B shows (Fourier-transform infrared spectroscopy) FTIR spectrum of the organosilicon functionalized SZO 1+TEPO.
Figure 9A:
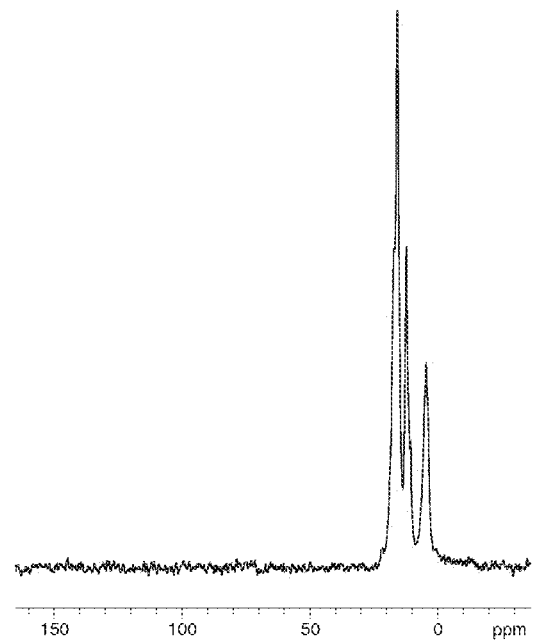
FIG. 9A shows a $^{13}$-C CP-MAS spectrum of the organosilicon functionalized SZO of Formula 1 shown in FIG. 5 +TEPO, spinning@10 kHz, 10 k scans.
Figure 9B:
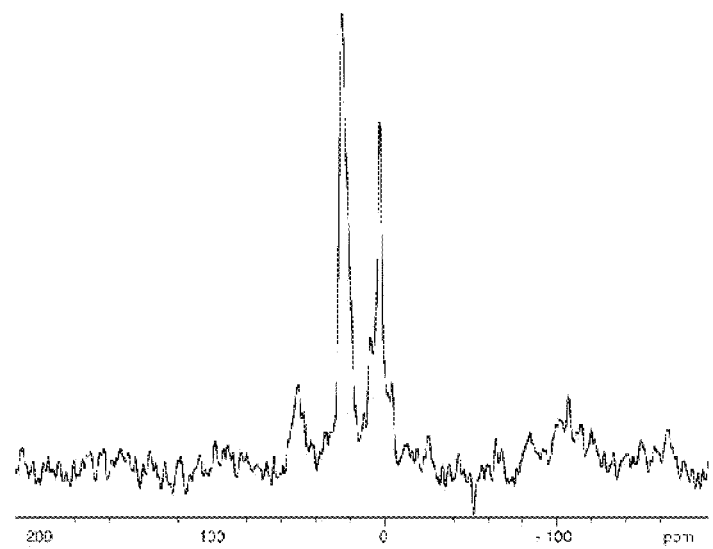
FIG. 9B shows a $^{29}$Si CP-MAS spectrum of the organosilicon functionalized SZO 1 shown in FIG. 5 +TEPO, spinning@8 kHz, 30 k scans.
Figure 10A:
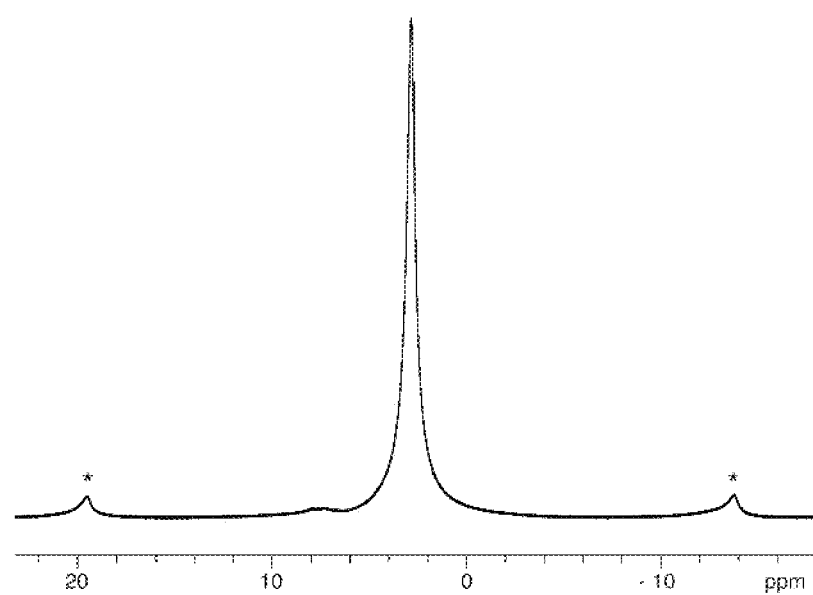
FIG. 10A illustrates $^1$H NMR spectrum of the organosilicon functionalized SZO of Formula 1 shown in FIG. 5 +TEPO spinning@10 kHz, 64 scans.
Figure 10B:
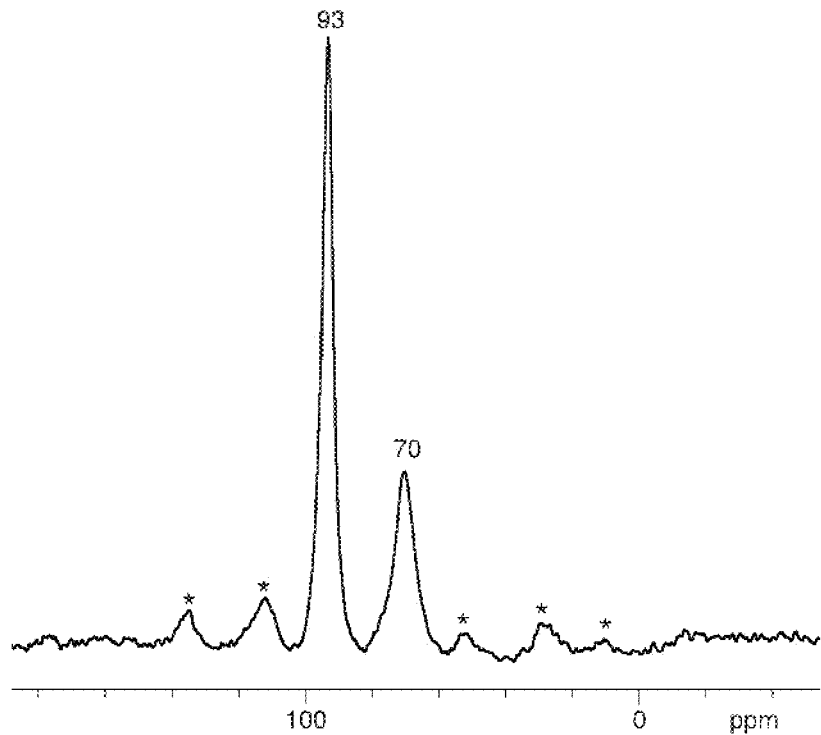
FIG. 10B illustrates $^{31}$P CP-MAS spectrum of the organosilicon functionalized SZO 1 shown in FIG. 5 +TEPO, spinning@10 kHz, 2 k scans. * in the figures indicate spinning sidebands.

A reaction between Compound 1 and TEPO was performed as schematically illustrated in FIG. 8A. In particular, pentane (0.5 ml) was condensed over 2.8 mg (22 μmol) of triethylphosphine oxide and 150 mg (21 μmol surface OH) of 1 at −196° C. The slurry was stirred for 30 minutes at room temperature, then dried en vacuo. FIG. 8B shows FTIR of 1+ TEPO. The $^{13}$-C CP-MAS, $^{29}Si$ CP-MAS, $^1H$ NMR and $^{31}P$ -CP-MAS of 1+TEPO were detected as illustrated in FIGS. 9A, 9B, 10A and 10B respectively.

It is noted that the $^{31}P\{^1H\}$ MAS NMR spectrum of 1. . . OPEt$_3$ contains two signals at 93 and 70 ppm, giving 46 values of 43 and 20 ppm, respectively as reported in Table 1 illustrated in FIG. 14

In particular, Table 1 in FIG. 14 contains the $^{31}P\{^1H\}$ MAS NMR chemical shift for the 1.OPEt$_3$, together with corresponding values for selected silicon Lewis acids for comparison. Neutral perhalogenated bis(catecolato)Si Lewis acids shift the $^{31}P$ signal by ~35 ppm in $C_6D_6$ solution. [Et$_3$Si][WCA], common intermediates in HDF reactions, forms $Et_3Si^+.OPEt_3$ and has $\Delta\delta$ of 43.4 ppm. These results indicate that 1 contains strong Lewis acid silicon on the SZO surface. The presence of two peaks in the $^{31}P$ MAS NMR spectrum of 1 is not surprising because the $^{29}Si$ CPMAS NMR spectrum of 1 shows that [TIPS][SZO], TIPS-$O_x$, and $SiO_x$ are present in 1.

Figure 6:
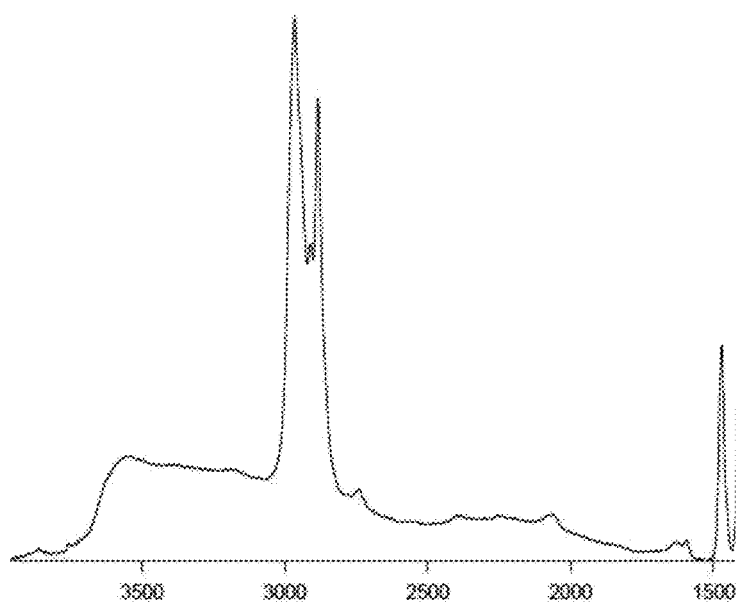
FIG. 6 illustrates the FTIR of the organosilicon functionalized SZO 1 shown in FIG. 5, as an exemplary embodiment of the solid organosilicon compound herein described.
Figure 7A:
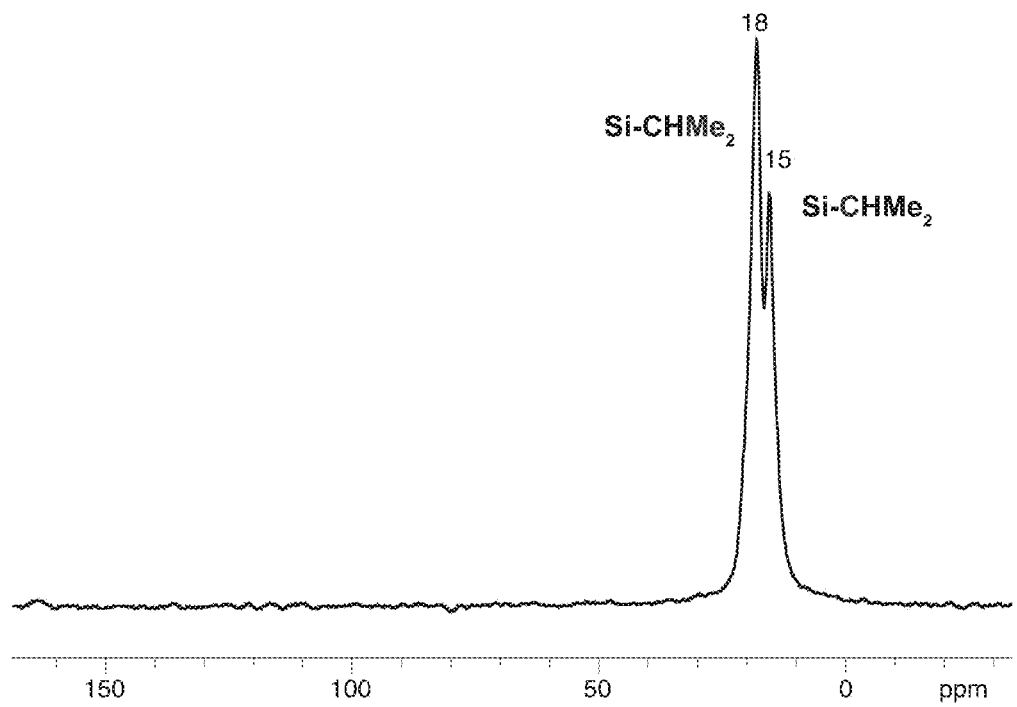
FIGS. 7A-B show solid state NMRs of organosilicon functionalized SZO 1. In particular.
Figure 7B:
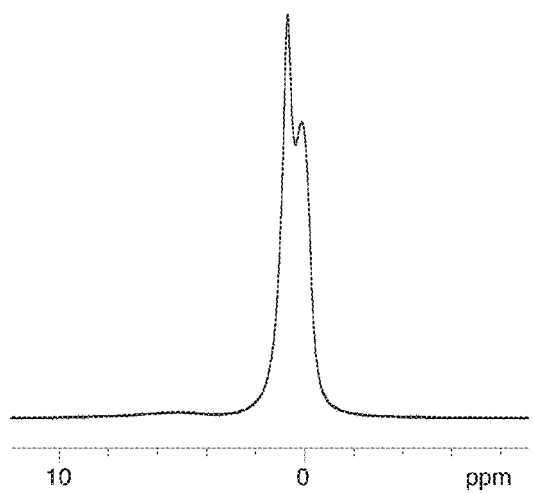

A further characterization of the exemplary organosilicon compound 1 was performed by FTIR, the results of which are illustrated in FIG. 6, by Solid state NMRs (see FIGS. 7A-B).

Example 3

The Reaction of Exemplary Allyltriisopropylsilane+ $Al_2O_3$ (2)

To test the generality of the HDF reaction with $R_3Si/$ oxides, exemplary TIPS/$Al_2O_3$ (2) was also prepared from the reaction of allyltriisopropylsilane and partially dehydroxylated alumina.

Figure 11A:
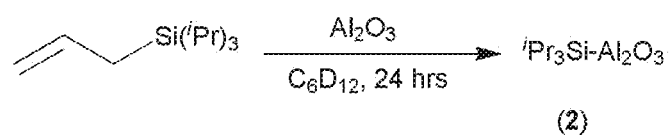
FIG. 11A illustrates a reaction scheme for the preparation of an exemplary moiety that can be used in solid organosilicon compound and/or complex of the disclosure and related methods and systems; in particular
Figure 11B:
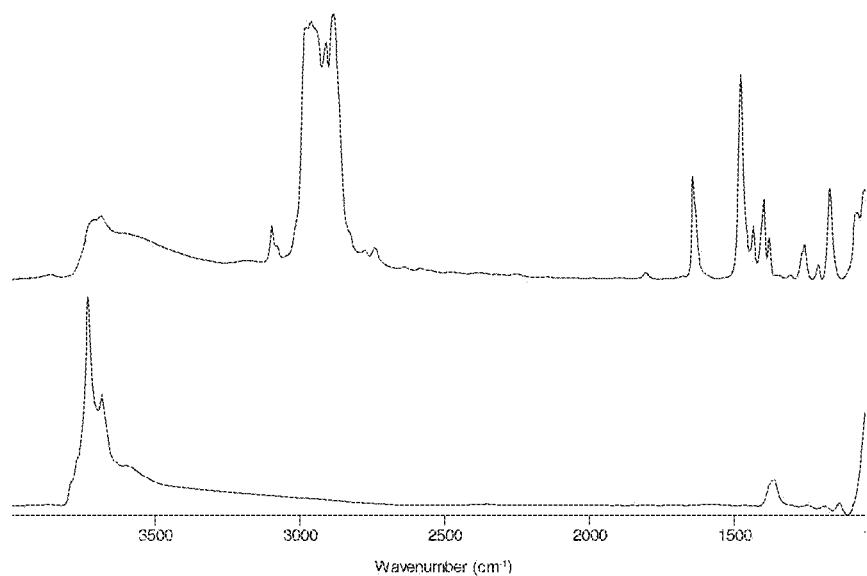

In particular, allyltriisopropylsilane (0.12 ml, 0.5 mmol) was added to a slurry of cyclohexane (0.5 ml) and $Al_2O_3$ (0.1 g, 0.09 mmol OH) in a teflon-sealed NMR tube. The tube was sealed and allowed to react for 24 hours. The white solid was washed with pentane (4×1 ml) and dried under vacuum. The propene released was measured by vacuum transferring the volatiles to a new teflon sealed NMR tube containing ferrocene as an internal standard. Propene: 0.17 mmol/g. This result and the FTIR (FIG. 11B) are consistent with the reaction of the allylsilane with surface OH groups. The $^{29}Si$ CPMAS spectrum is also consistent with this result, but the $^1H$ MAS and $^{13}$-C CPMAS NMR spectrum shows some allylsilane is not washed off with pentane and remains adsorbed on the surface.

Figure 12A:
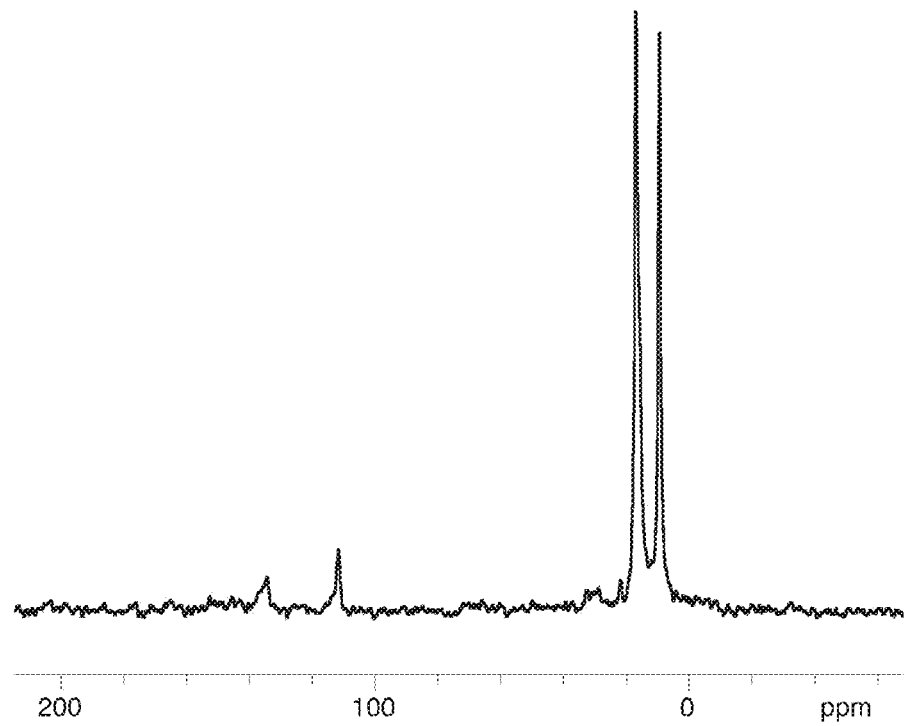
FIG. 12A illustrates a $^{13}$-C cross polarized magic angle spinning (CP-MAS) spectrum of the triisopropylsilane functionalized alumina $^i$Pr$_3$Si—Al$_2$O$_3$ (2) of FIG. 11A, spinning@8 kHz, 20 k scans.
Figure 12B:
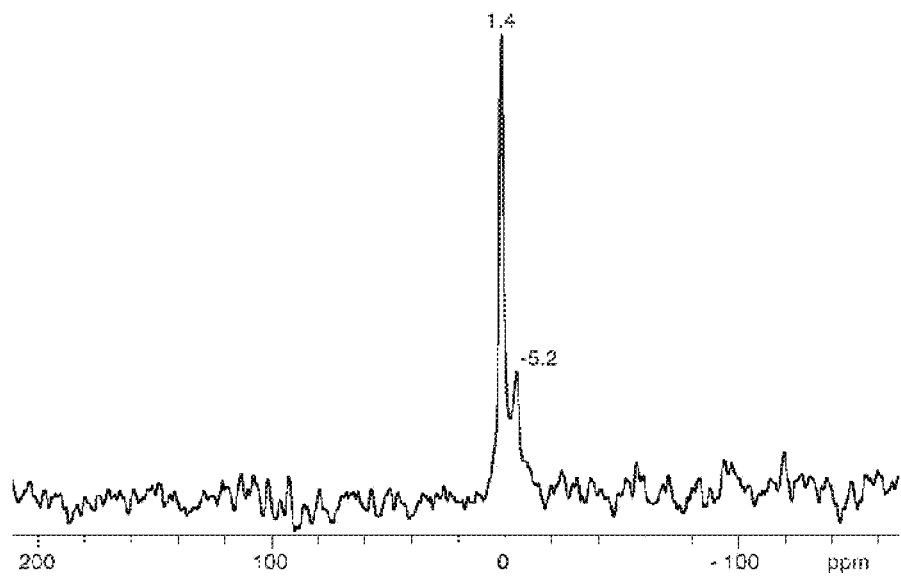
FIG. 12B illustrates $^{29}$Si CP-MAS spectrum of triisopropylsilane functionalized alumina $^i$Pr$_3$Si—Al$_2$O$_3$ (2) of FIG. 11A spinning@8 kHz, 30 k scans.
Figure 12C:
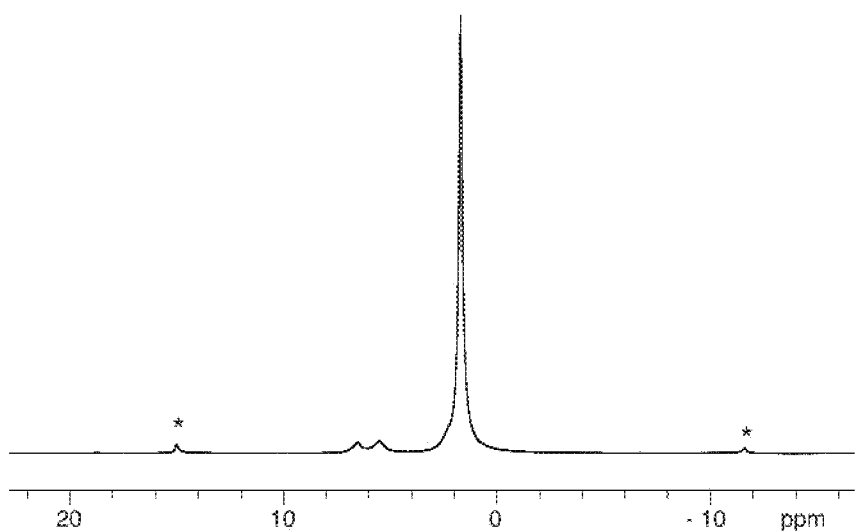
FIG. 12C illustrates the $^1$H magic angle spinning (MAS) of the triisopropylsilane functionalized alumina $^i$Pr$_3$Si—Al$_2$O$_3$ (2) of FIG. 11A, spinning@10 kHz, 64 scans. *=spinning sidebands.

To further characterize organosilicon compound (2), the $^{13}$-C CP-MAS $^{29}Si$ CP-MAS and $^1H$ MAS of 2 were measured as illustrated in FIGS. 12A, 12B and 12C, respectively.

Example 4

Figure 13A:
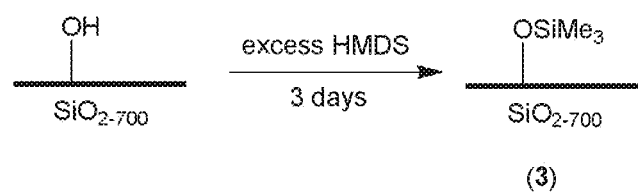
FIG. 13A illustrates the reaction scheme of passivation of SiO$_2$ which was obtained by dehydroxylating Aerosil-200 at 700° C. to form trimethylsilanated SiO$_2$ (3) providing an exemplary way to passivate the OH group on a SiO2 moiety of solid organosilicon compound and/or complex of the disclosure and related methods and systems.
Figure 13B:
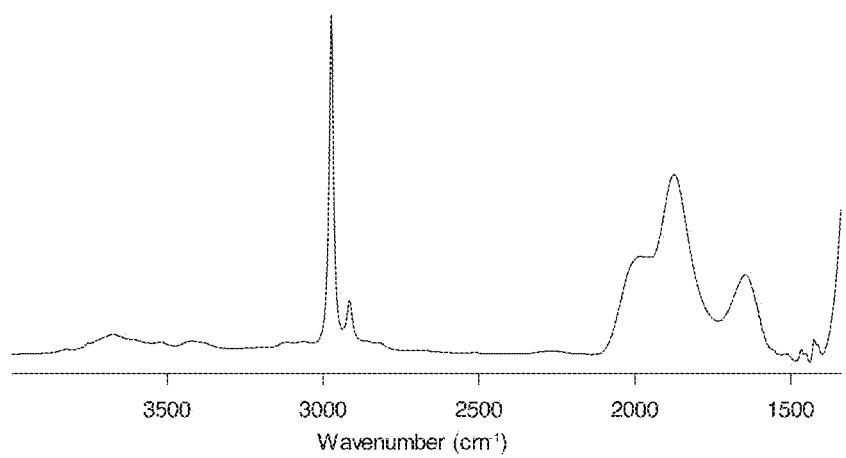
FIG. 13B shows the FTIR spectrum of the trimethylsilanated SiO$_2$ 3 formed as shown in FIG. 13A.
Figure 13C:
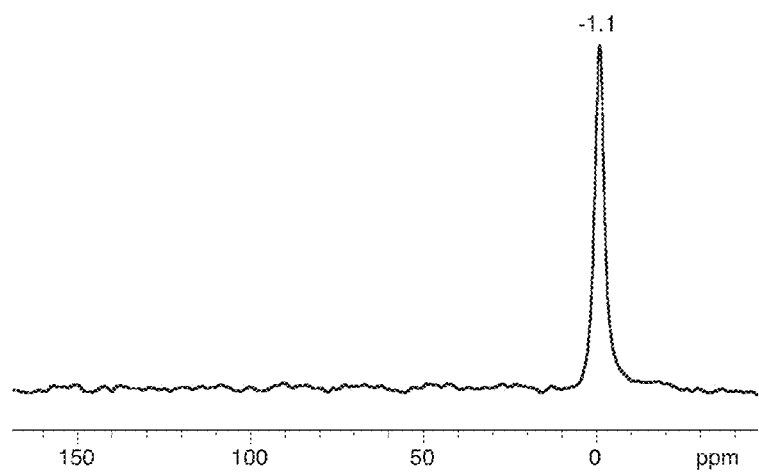
FIG. 13C shows solid state NMRs spectrum of the trimethylsilanated SiO$_2$ 3 of FIG. 13A, and in particular a $^{13}$-C CP-MAS NMR, spinning@8 kHz, 10 k scans.
Figure 13D:
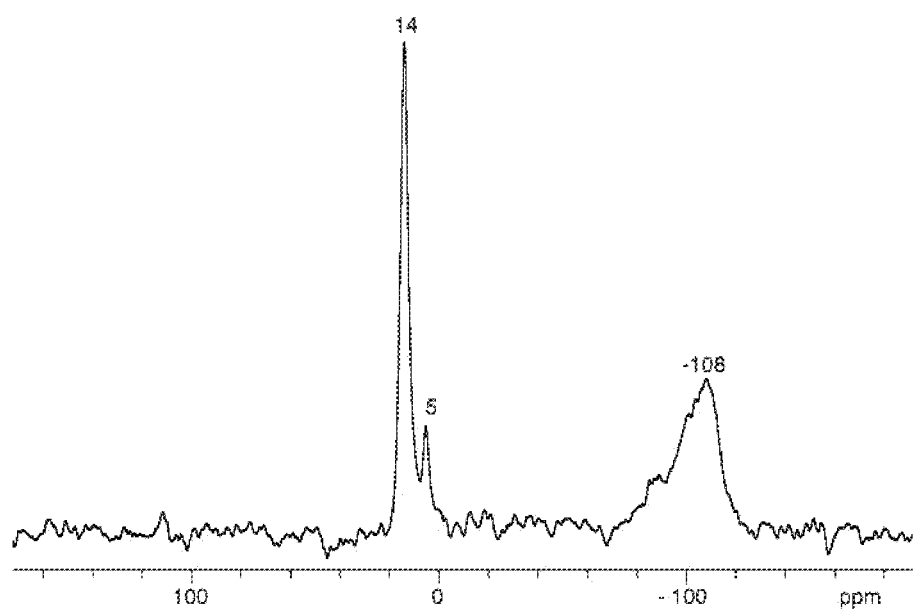
FIG. 13D shows solid state NMRs spectrum of trimethylsilanated SiO$_2$ 3 of FIG. 13A, in particular a $^{29}$Si CP-MAS NMR spectrum, spinning@8 kHz, 30 k scans.
Figure 13E:
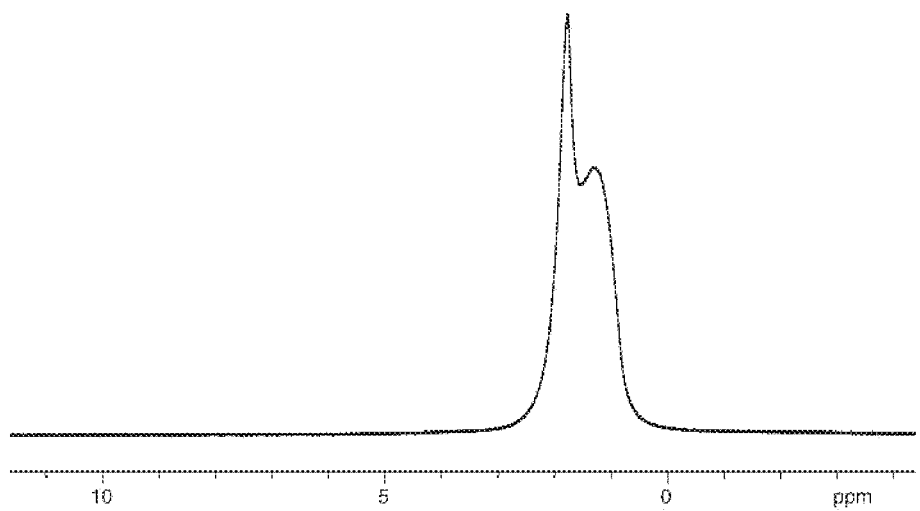
FIG. 13E shows an $^1$H NMR spectrum of the trimethylsilanated SiO$_2$ 3, of FIG. 13A spinning@8 kHz, 64 scans.
Figure 15:
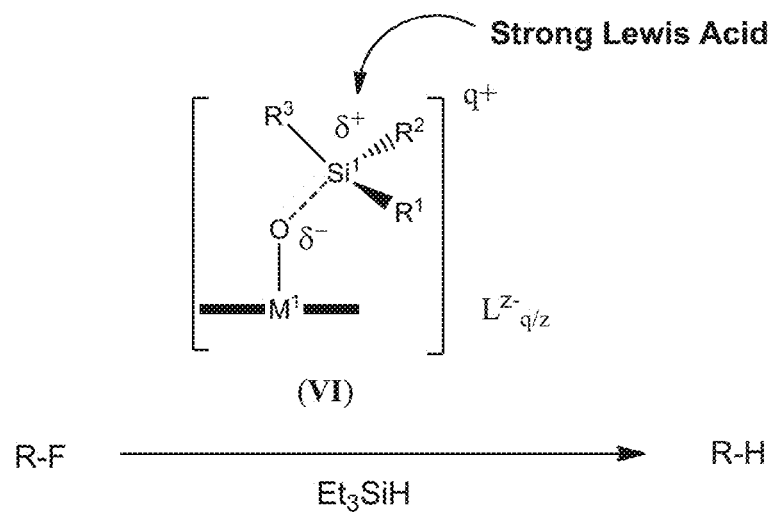
FIG. 15 illustrates a schematic representation of hydrodefluorination of fluorocarbon compound R—F to R—H catalyzed by exemplary organosilicon compound (VI) in the presence of triethylsilane Et$_3$SiH.

Passivation of $SiO_2$ (3):

Surface hydroxyl group in organosilicon compounds and complex herein described can be deactivated or kept as will be understood by a skilled person upon reading of the present disclosure. An exemplary passivation procedure was performed on $SiO_2$ (3) according to the reaction scheme illustrated in FIG. 13A.

TMS/$SiO_2$ (3) was prepared from the reaction of partially dehydroxylated silica and $HN(SiMe_3)_2$. The procedure was modified from reference 4. Aerosil-200 dehydroxylated at 700° C. (500 mg) was passivated with HMDS (2 mL), added by vacuum transfer. The wet solid was stirred for 3 days under static argon. The volatiles were removed en vacuo at room temperature for 3 hours and the dried sample was heated under dynamic vacuum ($10^{-6}$ torr) at 300° C. for 4 hours.

The resulting passivated $SiO_2$ (3) was characterized by FTIR of $^{13}$-C CP-MAS NMR, $^{29}Si$ CP-MAS NMR, and $^1H$ NMR, as illustrated in FIGS. 13B, 13C 13D and 13E, respectively.

The $^{29}Si$ CPMAS spectrum of both materials, TIPS/$Al_2O_3$ (2) and TMS/$SiO_2$ (3), contains signals at ~0 ppm, consistent with the formation of $R_3Si$—$O_x$ surface species. Both 2 and 3 are inactive in HDF of $C_6H_5CF_3$ in the presence of $Et_3SiH$ after 24 h at 80° C. as will be understood by a skilled person.

Example 5

Hydrodefluorination of Trifluorotoluene Catalyzed by Exemplary Organosilicon Compound 1

Figure 16A:
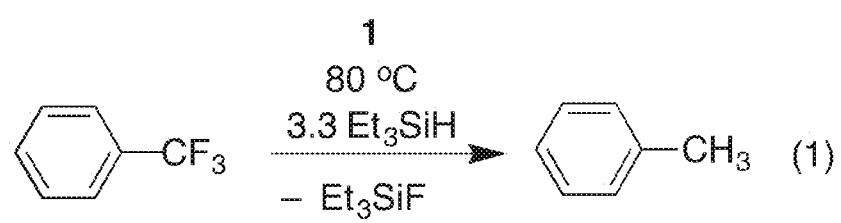
FIG. 16A illustrates the reaction scheme of hydrodefluorination of α,α,α-trifluorotoluene (benzotrifluoride) to toluene performed with exemplary organosilicon catalyst 1 illustrated in FIG. 5, in the presence of triethylsilane Et$_3$SiH.

A hydrodefluorination reaction of α,α,α-trifluorotoluene (benzotrifluoride) in the presence of catalyst 1 and triethylsilane was performed by organosilicon compound 1 according to the reaction scheme of hydrodefluorination shown in FIG. 16A.

In particular, in a $N_2$ filled glovebox, catalyst 1 (20 mg, 1 µmol active Si) was loaded into a teflon sealed NMR tube. Trifluorotoluene (0.06 ml, 0.5 mmol), triethylsilane (0.25 ml, 1.6 mmol), and $C_6F_6$ (internal standard) were added to the solid and the NMR tube was sealed. The NMR tube was removed from the glovebox and the reaction was heated for 2-12 hours at 80° C. The reaction was quenched by cooling to 0° C. and the solution was decanted away from the solid catalyst. The solution was analyzed by $^{19}F\{^1H\}$ NMR and GC to determine yields and TON. The same was repeated for 2 and 3 for comparison as they are not catalytically active, with the catalyst loadings listed in Table 2 of FIG. 16D.

Figure 16B:
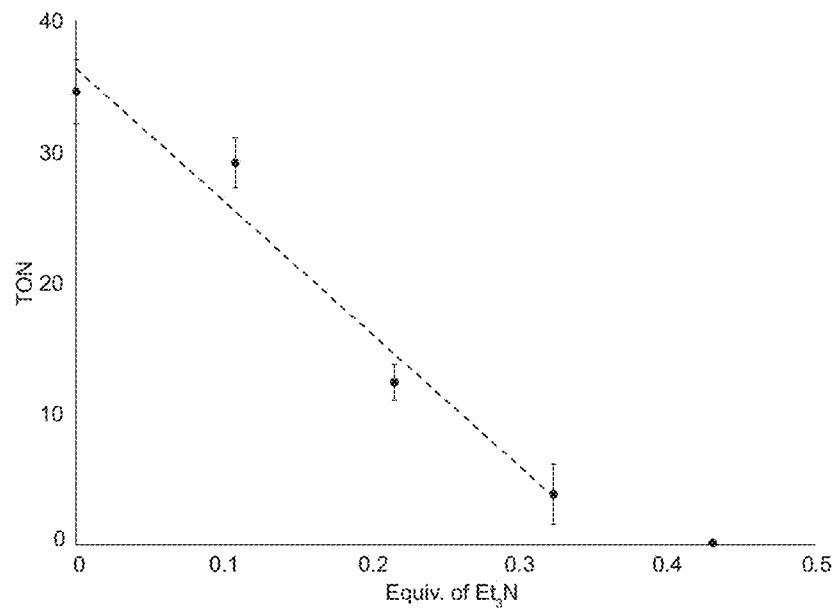
FIG. 16B shows a plot illustrating the reactivity of the organosilicon catalyst 1 shown in FIG. 5 in hydrodefluorination of benzotrifluoride in the presence of triethylamine (TON=turnover number=mol Et$_3$SiF/mol Si in 1) (see Example 8). The dashed line is a linear least squares regression of the activity data (y=92.2x−33.7; R$^2$=0.973).
Figure 16C:
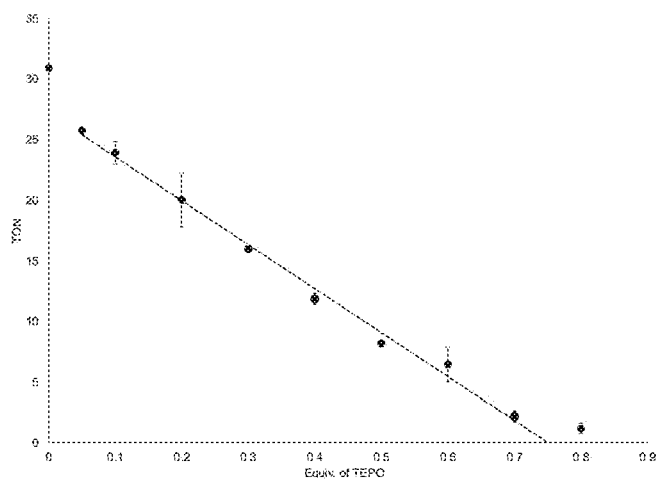
FIG. 16C shows a plot illustrating the reactivity of the organosilicon catalyst 1 shown in FIG. 5 in hydrodefluorination of trifluorotoluene (benzotrifluoride) in the presence of triethylphosphine oxide TEPO (TON=turnover number=mol Et$_3$SiF/mol Si in 1) (see Example 9).
Figures 16D, 16E:
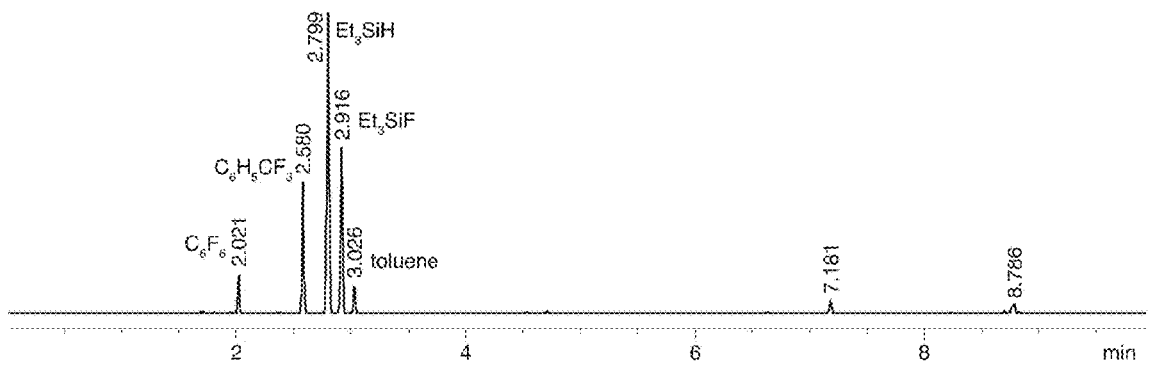
FIG. 16D shows Table 2 reporting the results of hydrodefluorination of fluorocarbon compounds catalyzed by catalyst 1 on various substrates concentrations and conditions as indicated in Table 2.
FIG. 16E shows a gas chromatograph (GC) of the mixture of hydrodefluorination reaction of benzotrifluoride catalyzed by catalyst 1 whose results are shown in FIG. 16C.

The results shown in Table 2 of FIG. 16D confirm that while compounds 2 and 3 had no detectable activity (0% conversion) for hydrodefluorination reaction, while compound 1 showed percentage conversion from 42% to >99% for different substrates at different concentrations as shown in Table 2.

In the illustration of FIG. 16D the turnover number (TON) was calculated based on the number of active sites in 1 from the poisoning study described above. 1 has a maximum TON of 680 in the HDF of neat $Et_3SiH/C_6H_5CF_3$ mixtures after 1 h at 80° C. (Table 2, entry 1). For comparison, $[Et_3Si][B(C_6F_5)_4]$ catalyzes the HDF reaction of neat $Et_3SiH/C_6H_5CF_3$ mixtures with a TON of 126, (Scott, V. J.; Celenligil-Cetin, R.; Ozerov, O. V. J. Am. Chem. Soc. 2005, 127, 2852-2853) and $[Et_3Si][CB_{11}H_5Cl_6]$ catalyzes this reaction with a TON of 2000 in the presence of o-dichlorobenzene cosolvent. (Douvris, C.; Nagaraja, C. M.; Chen, C. H.; Foxman, B. M.; Ozerov, O. V. J. Am. Chem. Soc. 2010, 132, 4946-4953) However, the homogenous reactions are active at room temperature, whereas 1 shows insignificant activity below ~60° C. Heterogeneous catalysts for the HDF reaction are rare. $AlCl_xF_{3-x}$, a very strong solid Lewis acid, catalyzes the HDF of $C_6H_5CF_3$ under similar conditions (TON=15, 70° C., 7 d), (Ahrens, M.; Scholz, G.; Braun, T.; Kemnitz, E. Angew. Chem. Int. Ed. 2013, 52, 5328-5332; Angew. Chem. 2013, 125, 5346-5440) albeit with lower TON and slower rates than 1.

At 120° C. 1 also is active in HDF of neat $Et_3SiH/C_6F_5CF_3$ to form $C_6F_5CH_3$ (TON=190, 504 h), though at much slower rates than benzotrifluoride. 1-Adamantylfluoride is more reactive in HDF than $C_6F_5CF_3$ with 1, giving a TON of 340 after 24 h at 25° C. 1 does not catalyze the HDF of perfluorohexane or hexafluorobenzene at elevated temperatures.

Figure 16F:
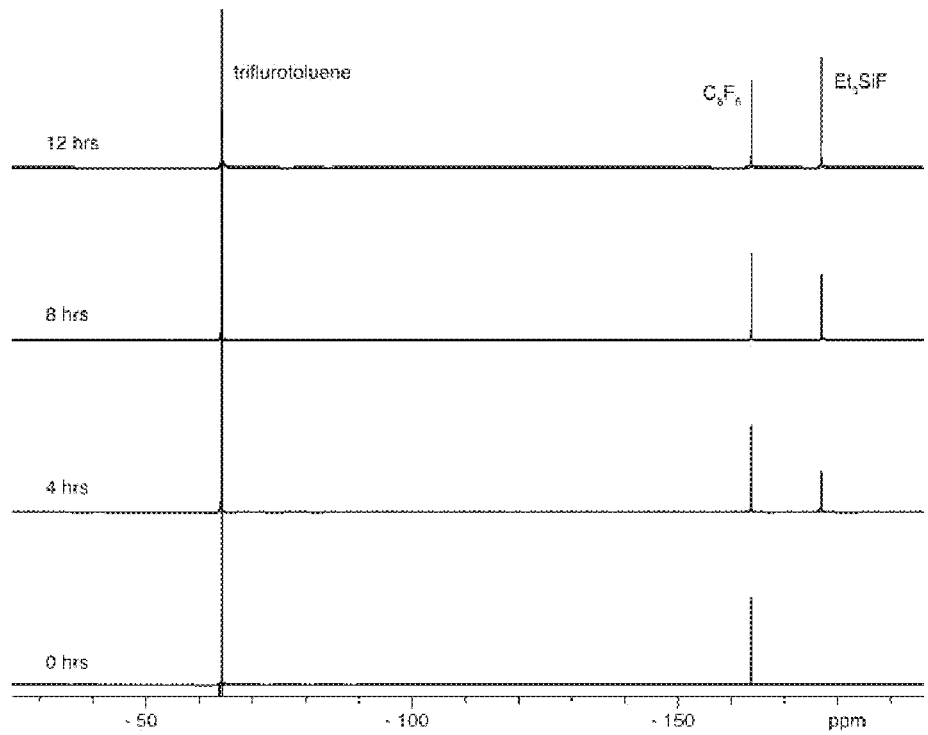
FIG. 16F shows solution NMRs of the HDF reaction mixture of trifluorotoluene with catalyst 1 shown in FIG. 16A over a period of 12 hours.
Figure 16G:
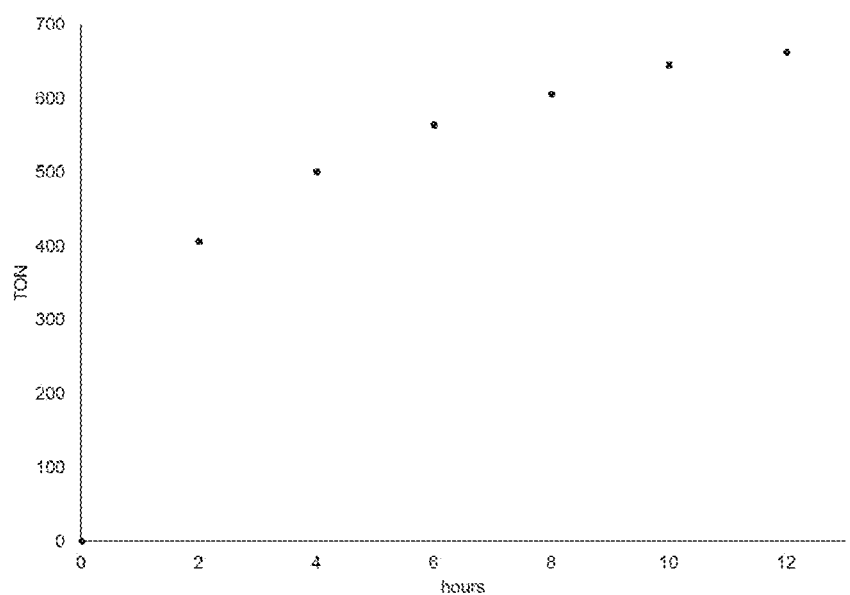
FIG. 16G shows Turnover Number (TON) for C—F activation of the reaction shown in FIG. 16A over time as measured by $^{19}$F{$^1$H} NMR and GC.

The reaction of α,α,α-trifluorotoluene (benzotrifluoride) in the presence of catalyst 1 and triethylsilane was monitored over time by Gas Chromatography (GC) and by solution NMRs and the results are illustrated in FIG. 16E and FIG. 16F respectively. FIG. 16G shows TON for C—F activation over time as measured by $^{19}F\{^1H\}$ NMR and GC.

The reactivity of 1 in hydrodefluorination of benzotrifluoride was also performed in the presence of triethylamine and the results are shown in FIG. 16B.

Initial studies showed that 1 reacts with 330 equiv benzotrifluoride (1500 equiv. of C—F) at 80° C. in the presence of excess Et$_3$SiH to give TIPSF, Et$_3$SiF, toluene, and Friedel-Crafts products (eq 1).(Douvris, C.; Nagaraja, C. M.; Chen, C. H.; Foxman, B. M.; Ozerov, O. V. J. Am. Chem. Soc. 2010, 132, 4946-4953) Contacting 1 with 1 equiv of Et$_3$N/Si results in negligible HDF activity, indicating that Et$_3$N poisons the Lewis acidic [TIPS][SZO] present in 1. A shown in FIG. 16B, the activity of 1 in the HDF of benzotriflouride at 80° C. decreases linearly in the presence of titrated amounts of Et$_3$N (FIG. 16B). This analysis indicates that 37% of the sites in 1 are active in this reaction, which is consistent with the presence of reactive [TIPS][SZO] and unreactive TIPS—O$_x$ observed in the $^{29}$Si CPMAS NMR spectra shown in FIG. 5, panel b.

Example 6

Hydrodefluorination of Octafluorotoluene with Exemplary Compound 1

Figure 17A:
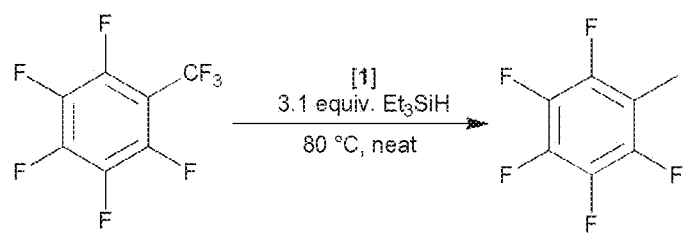
FIG. 17A illustrates the reaction scheme of hydrodefluorination of octafluorotoluene with exemplary organosilicon catalyst 1.

A hydrodefluorination reaction of octafluorotoluene in the presence of catalyst 1 and triethylsilane was performed by organosilicon compound 1 according to the reaction scheme of hydrodefluorination shown in FIG. 17A.

In particular, in a N$_2$ filled glovebox, catalyst 1 (50 mg, 2.4 µmol active Si) was loaded into a teflon sealed NMR tube. Octafluorotoluene (0.03 ml, 0.2 mmol), triethylsilane (0.12 ml, 0.75 mmol), and C$_6$F$_6$ (internal standard) were added to the solid and the NMR tube was sealed. The NMR tube was removed from the glovebox and the reaction was heated for 3 weeks at 120° C. The reaction was monitored by $^{19}$F {$^1$H} NMR. After the reaction stopped, it was cooled to room temperature and the solution was decanted away from the solid catalyst. The solution was analyzed by GC.

The results illustrated in FIGS. 17A to 17D show a selective defluorination of the sp3C—F on the octafluorotoluene.

Figure 17B:
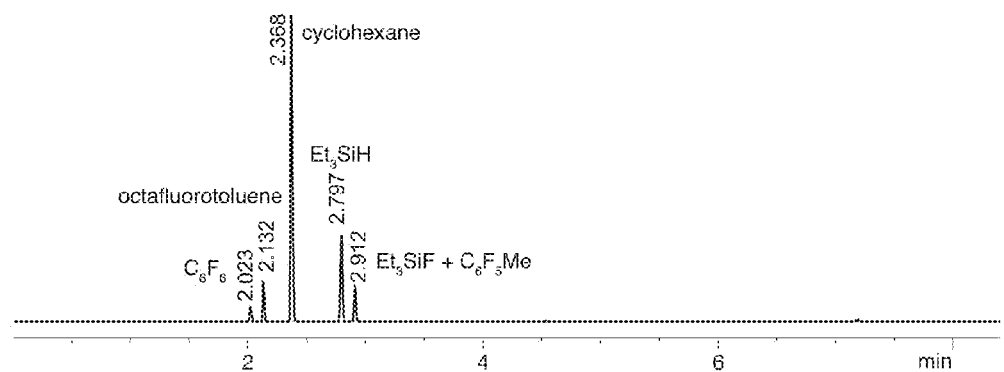
FIG. 17B shows the GC of the HDF of octafluorotoluene with exemplary organosilicon 1 shown in FIG. 17A.
Figure 17C:
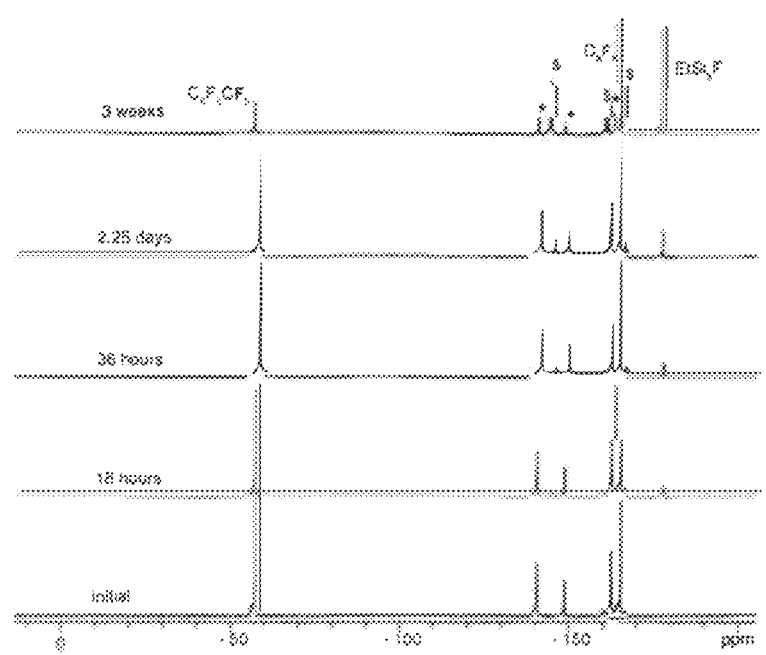
FIG. 17C shows solution NMRs of the HDF of octafluorotoluene at 120° C. with the exemplary organosilicon 1 shown in FIG. 17A over time; *=starting material and $=2,3,4,5,6-pentaflurotoluene.
Figure 17D:
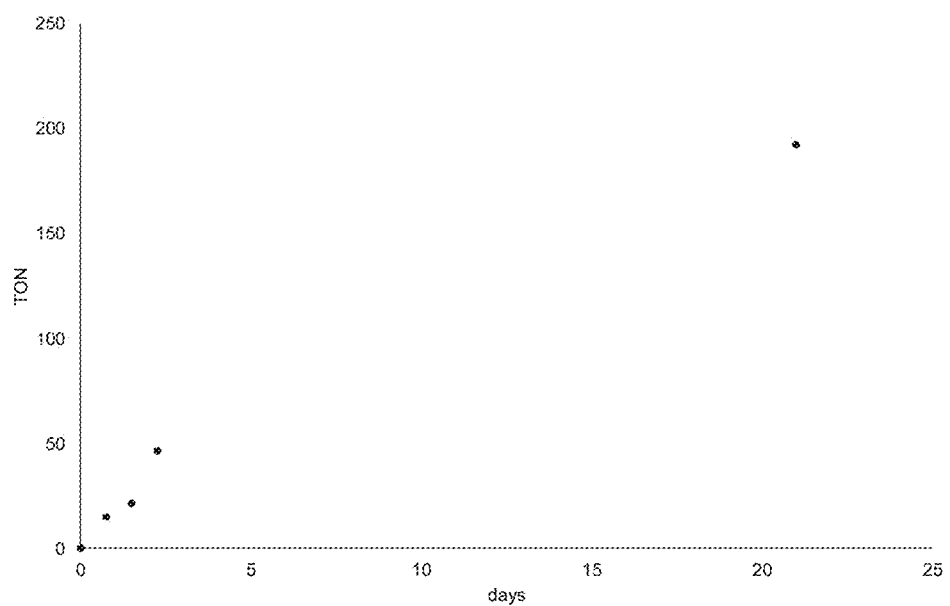
FIG. 17D shows TON for C—F activation of the HDF of octafluorotoluene at 120° C. with with exemplary organosilicon 1 shown in FIG. 17A over time as measured by $^{19}$F{$^1$H} NMR.

This result is apparent from the GC spectrum of FIG. 17B, the solution NMRs of the HDF of FIG. 17C and the TON for C—F activation over time as measured by $^{19}$F{$^1$H} NMR of FIG. 17D as will be understood by a skilled person.

Therefore, these results confirm the reactivity of 1 in hydrodefluorination reaction of octafluorotoluene.

Example 7

Hydrodefluorination of 1-fluoroadamantane

Figure 18A:
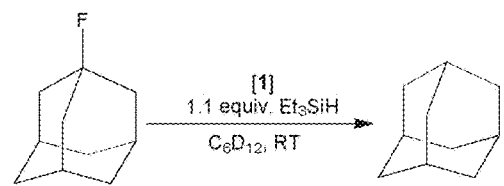
FIG. 18A illustrates the reaction scheme of hydrodefluorination of 1-fluoroadamantane with organosilicon catalyst 1.

A hydrodefluorination reaction of octafluorotoluene in the presence of catalyst 1 and triethylsilane was performed by organosilicon compound 1 according to the reaction scheme of hydrodefluorination shown in FIG. 18A.

In particular, in a glovebox, catalyst 1 (20 mg, 1 µmol active Si) was loaded into a teflon sealed NMR tube. Fluoroadamantane (60 mg, 0.4 mmol), triethylsilane (0.07 ml, 0.44 mmol), C$_6$D$_{12}$ (0.25 ml), and C$_6$F$_6$ (10 µl, 0.087 mmol) were added to the solid and the NMR tube was sealed. The NMR tube was removed from the glovebox and the reaction was monitored by $^{19}$F{$^1$H} NMR while reacting at room temperature over 24 hours. The solution was analyzed by GC after the reaction.

Figure 18B:
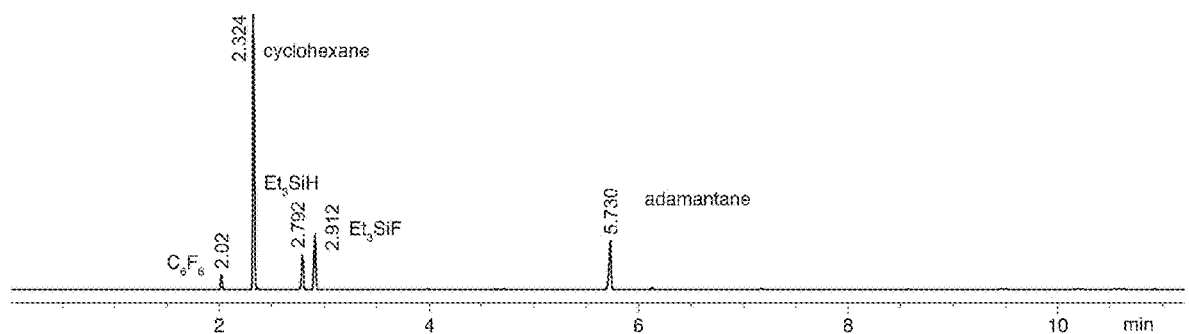
FIG. 18B shows GC of the HDF of 1-fluoroadamantane with exemplary organosilicon 1 shown in FIG. 18A.

The results show in FIG. 18B shows the defluorination occurred on the tertiary C—F of the 1-fluoroadamantane.

Figure 18C:
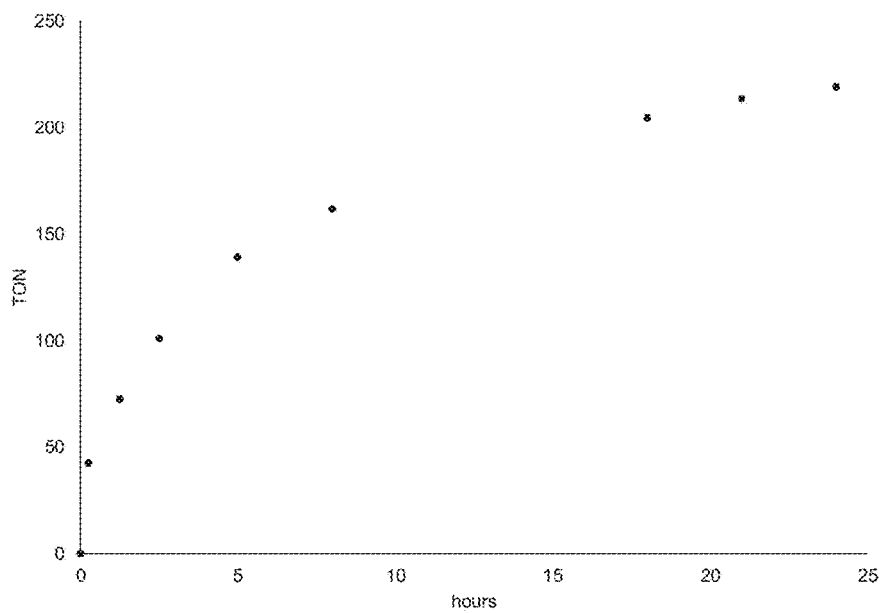
FIG. 18C shows TON of the HDF of 1-fluoroadamantane with exemplary organosilicon 1 shown in FIG. 18A over time at room temperature as measured by $^{19}$F{$^1$H} NMR.
Figure 18D:
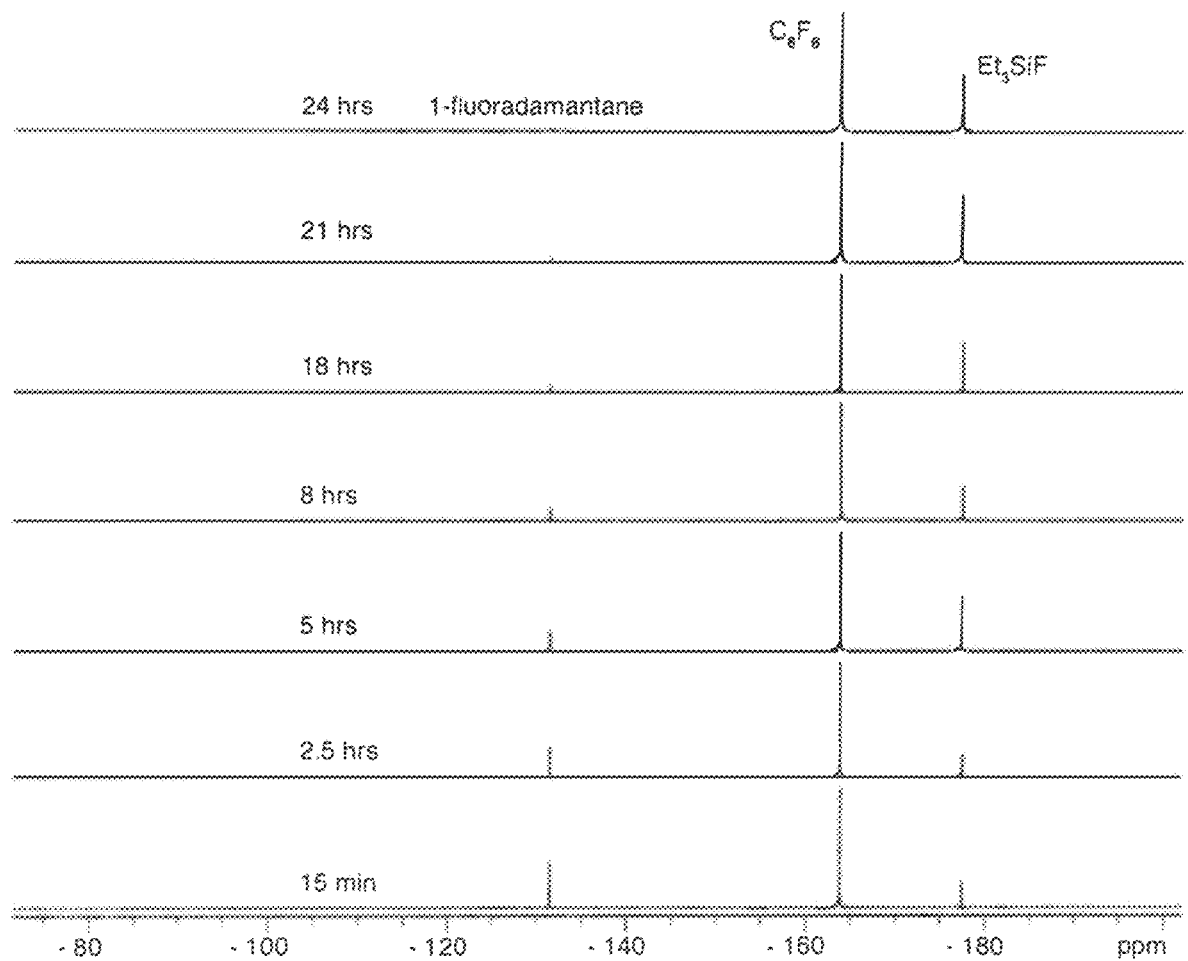
FIG. 18D shows solution $^{19}$F{$^1$H} NMRs of the HDF of 1-fluoroadamantane with exemplary organosilicon 1 shown in FIG. 18A over time. It is noted that not all of the 1-fluoroadamantane was dissolved at the beginning of the reaction.

The reactivity was also confirmed by TON of the HDF of 1-fluoroadamantane as measured by $^{19}$F{$^1$H} NMR (FIG. 18C). and by solution $^{19}$F{$^1$H} NMRs of the HDF of 1-fluoroadamantane with catalyst 1 over time (FIG. 18D). It is noted that not all of the 1-fluoroadamantane was dissolved at the beginning of the reaction.

Therefore, these results confirm the catalytic activity of organosilicon compound 1 in hydrodefluorination reaction of 1-fluoroadamantane.

Example 8

Poisoning Study in Et$_3$N

Figure 19A:
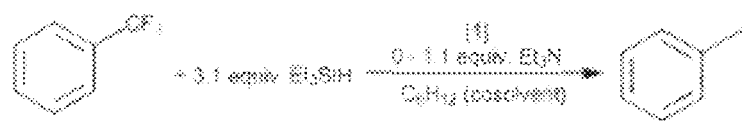
FIG. 19A illustrates a reaction scheme for catalyst poisoning in the hydrodefluorination of benzotrifluoride catalyzed by organosilicon compound 1 in the presence of triethylsilane and triethyl amine (Et₃N) as described in Example 8.

A poison study of compound 1 was performed in accordance with the reaction scheme illustrated in FIG. 19A.

In particular, cyclohexane (0.1, 0.09, 0.08, 0.07, or 0.06 ml) and a solution of 1.4 M triethylamine in cyclohexane (0, 0.01, 0.02, 0.03, or 0.04 ml respectively) were added to catalyst 1 (100 mg, 13 µmol OH) in a teflon sealed NMR tube to a constant volume of 0.1 ml at 80° C. The slurry was allowed to equilibrate for 10 min then triethylsilane (81 µl, 0.5 mmol) and trifluorotoluene (19 µl, 0.15 mmol) were added to the slurry. The reaction was heated to 80° C. for 1 hour then quenched by cooling to 0° C. and were diluted with cyclohexane (0.2 ml) prior to analysis by GC or were analyzed directly by $^{19}$F{$^1$H} NMR with an internal standard of hexafluorobenzene.

The study confirms that the reactivity of the compound was inactivated by Et3N.

Example 9

Poisoning Study in TEPO

Figure 19B:
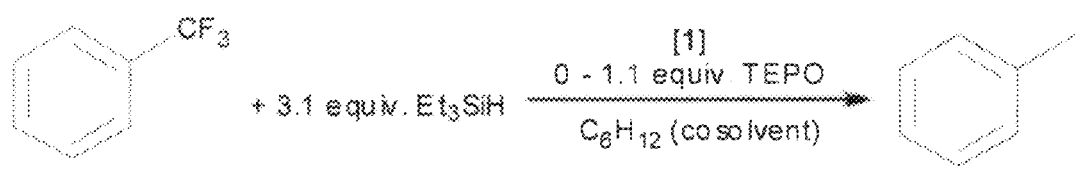
FIG. 19B illustrates a reaction scheme for catalyst poisoning in the hydrodefluorination of benzotrifluoride catalyzed by organosilicon compound 1 in the presence of triethylsilane and TEPO as described in Example 9.
Figure 20:
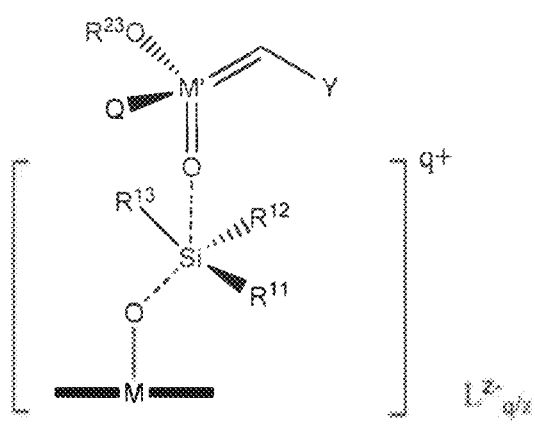
FIG. 20 illustrates a schematic representation of an organosilicon exemplary complex of Formula (IX) having a silylium on a solid oxide of element M complexed to organometallic compound of transition metal M'.
Figure 21A:
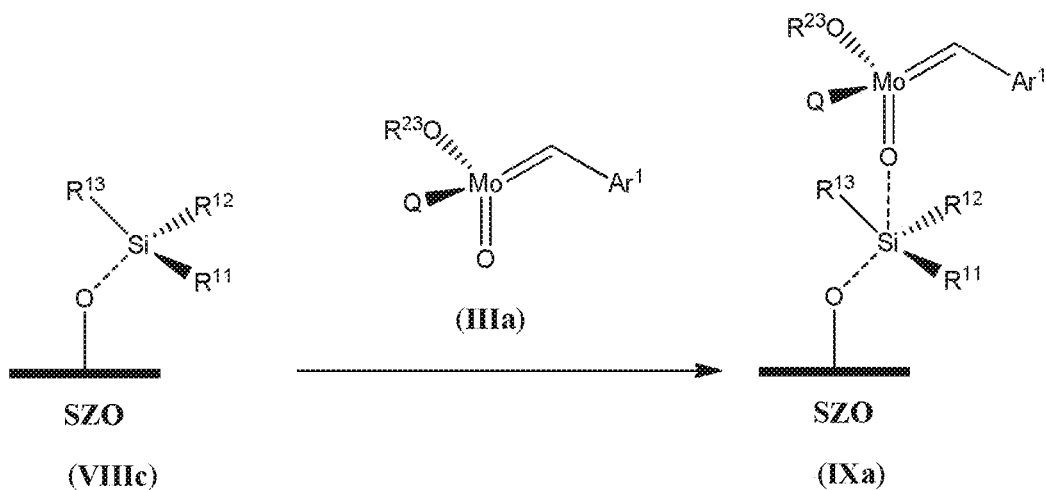
FIG. 21A illustrates a schematic representation of an exemplary formation of organosilicon complex of Formula (IXa) by complexation of organomolybdenum compound (IIIa) to organosilicon compound (VIIIc).
Figure 21B:
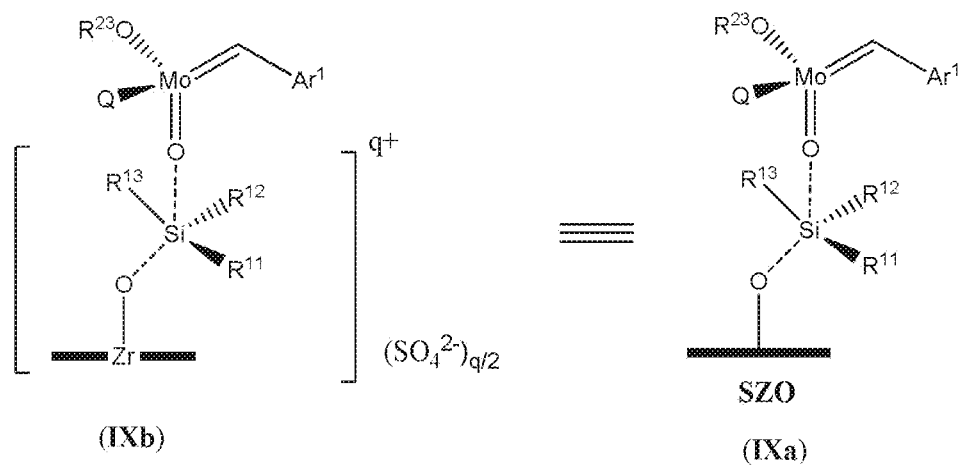
FIG. 21B illustrates a schematic representation of the structure of an exemplary organosilicon complex of Formula (IXb) on zirconium oxide with sulfate counter anion which is abbreviated as an equivalent structure of Formula (IXa) showing SZO.
Figure 21C:
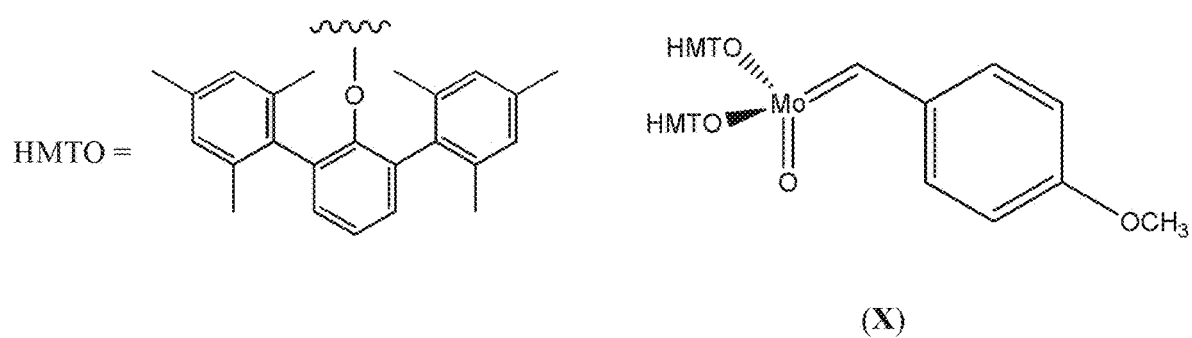
FIG. 21C illustrates a schematic representation of the structure of an exemplary organometallic compound Mo1 of Formula (X) in which a molybdenum-oxo-alkylidene is coordinated by two 2,6-bis(2,4,6-trimethylphenyl)phenoxy (HMTO) ligands.

A poison study of compound 1 was performed in accordance with the reaction scheme illustrated in FIG. 19B.

Cyclohexane (0-0.1 ml) and a solution of 0.07 M TEPO in cyclohexane (0-0.1 ml) were added to catalyst 1 (50 mg, 7 µmol OH) in a teflon sealed NMR tube to achieve a constant volume of 0.1 ml. The slurry was allowed to equilibrate for 30 min at room temperature. Triethylsilane (81 µl, 0.5 mmol), trifluorotoluene (19 µl, 0.15 mmol), and hexafluorobenzene (internal standard) were added to the slurry. The reaction was sealed and heated to 80° C. for 30 minutes then quenched by cooling to 0° C. The reactions were analyzed by $^{19}$F{$^1$H} NMR to determine TON by quantifying Et$_3$Si—F relative to C$_6$F$_6$ internal standard. The short reaction time and the high catalyst loading (Si:C—F=1:36) were used to ensure 1 maintains activity over the course of the experiment. Under these conditions, in the absence of TEPO, 1 catalyzes 32 turnovers in 30 minutes, and 45 turnovers after 1 hour; indicating that 1 is active over the course of the experiment by TEPO.

Example 10

Grafting the Mo-oxo-alkylidene on TIPSi-SZO$_{300}$

Figures 22, 23:
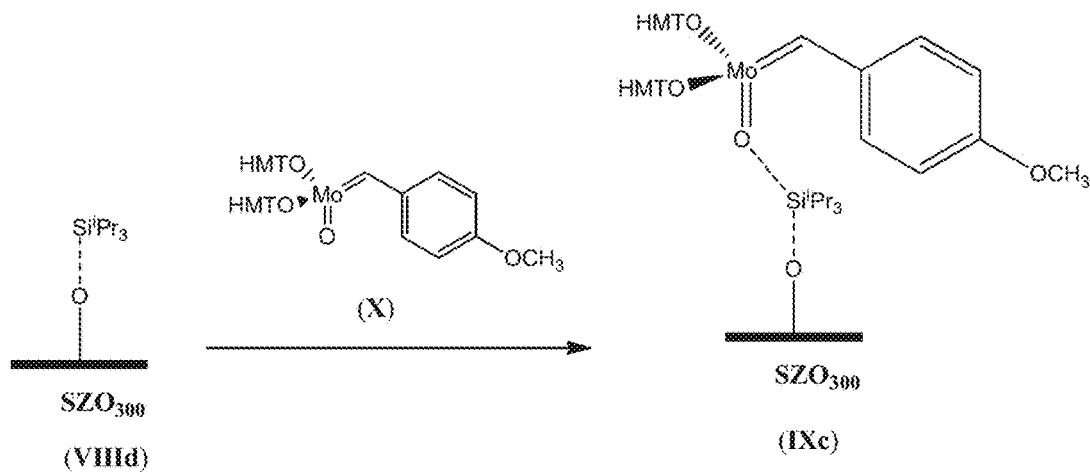
FIG. 22 illustrates the scheme of an exemplary grafting reaction the organometallic compound Mo1 of Formula (X) on TIPSi-SZO$_{300}$ for the formation of an exemplary organosilicon complex, a catalyst (TIPSi-SZO$_{300}$-Mo1) having Formula (IXc) in accordance with the present disclosure.
FIG. 23 shows Table 4 reporting a metathesis activity in an open vial, neat at RT, of TIPSi-SZO$_{300}$-Mo1 an exemplary organosilicon complex of Formula (IXc) (illustrated in FIG. 22).

An exemplary formation of an organosilicon complex of the disclosure was performed by grafting a Mo-oxo-alkylidene on SZO$_{300}$ according to the reaction scheme of FIG. 22.

In particular all grafting reactions were carried out in double-Schlenk flasks connected by a frit filter using high vacuum Schlenk lines. 800 mg of SZO$_{300}$ (0.13 mmol$_{-OH}$/g) and 46 mg of Mo1 (0.5 equiv based on the —OH loading of SZO$_{300}$) inside an argon-filled glovebox. $^1$H NMR spectrum of the was shows unreacted Mo1 and free HMTOH. Quantitative analysis of the $^1$H NMR spectrum with the aid of 1,3,5-trimethoxybenznene as the internal standard shows 0.054 mmol of free HMTOH per gram of SZO$_{300}$ (possibly corresponding to grafted molybdenum complexes). Elemental analysis: C: 2.24% H: 0.3% Mo: 0.39% (C: 1.92% H: 0.16% Mo: 0.48% calculated based on free HMTOH released during grafting).

The grafting procedure was performed as described above using 500 mg of TIPSi-SZO$_{300}$ (0.1 mmol$_{Si}$/g) and 36 mg of Mo1 (0.8 equiv based on silicon loading) were placed in a double-Schlenk flask, where the two flasks were separated by a fritted filter and one side could be connected to a high vacuum line. About 5 ml of benzene was vacuum transferred at 77 k and the heterogeneous mixture was allowed to stir for 4 hours during which the support turns dark purple. The supernatant was filtered off to the other arm of double-Schlenk and the molybdenum containing material was washed two times by condensing the solvent at 77 k, washing the grafted material for 5 minutes and filtering the solvent back to the other arm of double-Schlenk. The molybdenum containing SZO$_{300}$ was dried in vacuo. The molybdenum containing material was stored in the glovebox. Elemental analysis: C: 1.99% H: 0.34% Mo: 0.13%.

Example 11

Figure 25:
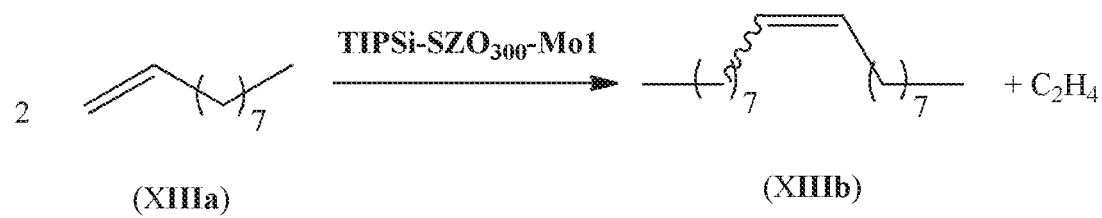
FIG. 25 shows a reaction scheme for the metathesis of 1-decene (XIIIa) as catalyzed by the exemplary organosilicon complex TIPSi-SZO$_{300}$-Mo1 in accordance with the present disclosure to form homocoupled olefin (XIIIb) with formation of ethylene with the results presented in Table 4.
Figure 26:
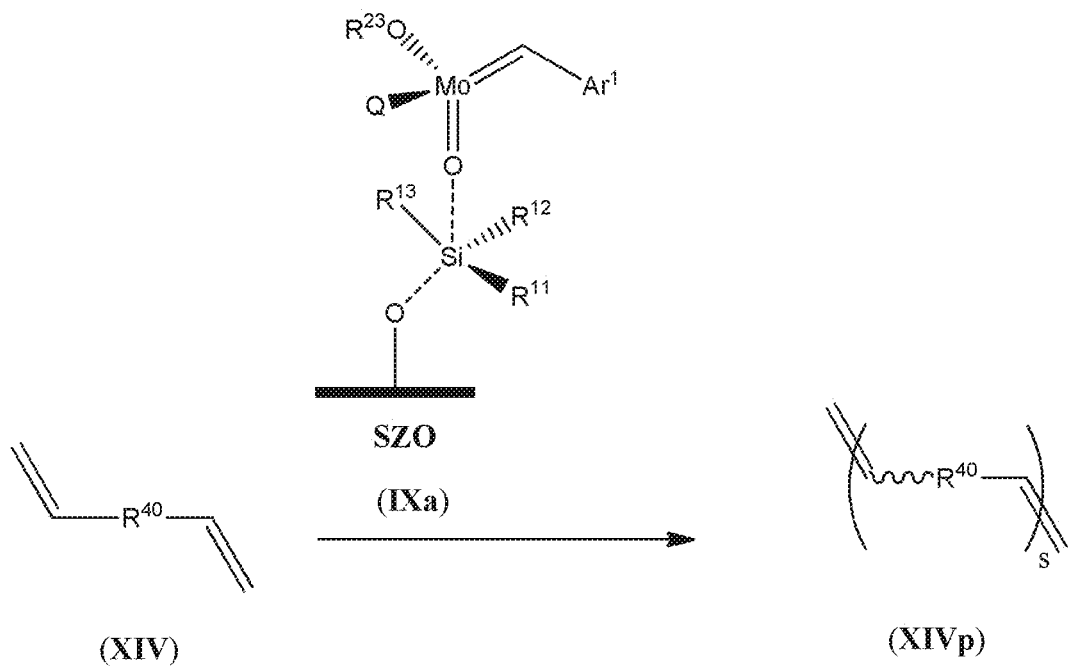
FIG. 26 shows a reaction scheme for the metathesis polymerization of acyclic diolefin of Formula (XIV) to form a polymer of Formula (XIVp) in the presence of solid organosilicon complex (IXa).
Figure 27:
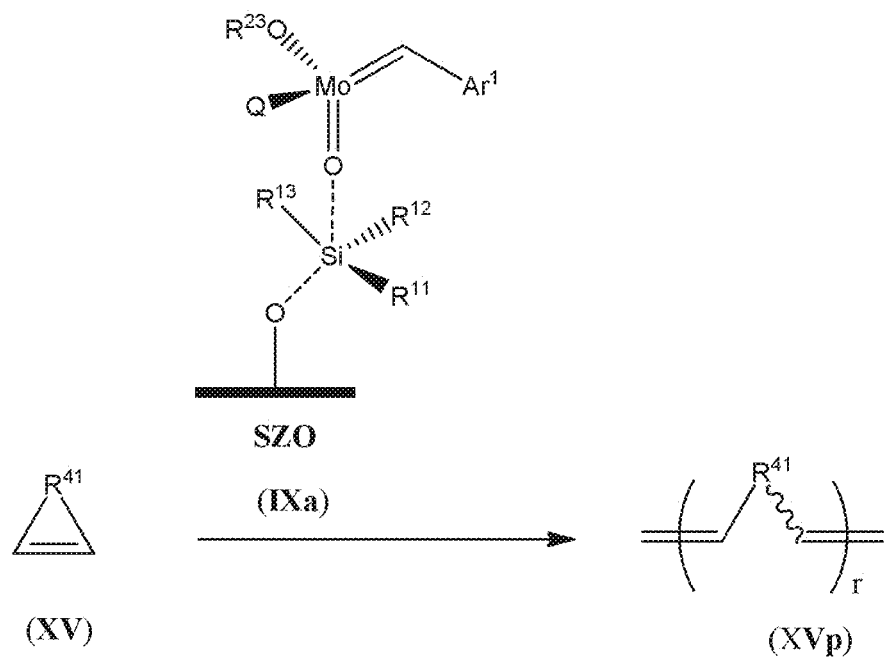
FIG. 27 shows a reaction scheme for the ring-opening metathesis polymerization of cyclic olefin of Formula (XV) to form a polymer (XVp) in the presence of solid organosilicon complex (IXa).

Metathesis Activity of SZO$_{300}$-Mo1 and TIPSi-SZO$_{300}$-Mo1 in Homocoupling of 1-decene Metathesis activity of the exemplary TIPSi-SZO$_{300}$-Mo1 synthesized as reported in Example 10 was detected by the metathesis of 1-decene (XIIIa) catalyzed by TIPSi-SZO$_{300}$-Mo1 to form homocoupled olefin (XIIIb) with formation of ethylene, performed according to the reaction scheme in FIG. 25.

In particular catalytic trials were performed in an open vial in the glovebox as follows. A known amount of the heterogeneous catalyst, typically 50 mg, was placed in a vial equipped with a stir bar. 1350 μl of 1-decene (1 g) was added and the mixture was allowed to stir. A known volume was taken periodically and analyzed by $^1$H NMR spectroscopy against 1,3,5-trimethoxybenzene as the internal standard. Carrying out the catalytic reaction in an open vial results in higher activity as the byproduct ethylene escapes from the mixture (avoiding back reaction and/or reduction of molybdenum).

Table 4 in FIG. 23 shows the related results wherein TOF's (h$^{-1}$) are based on the mmol Mo per gram on surface obtained from grafting reactions and measuring the amount of unreacted Mo1.

Figure 24:
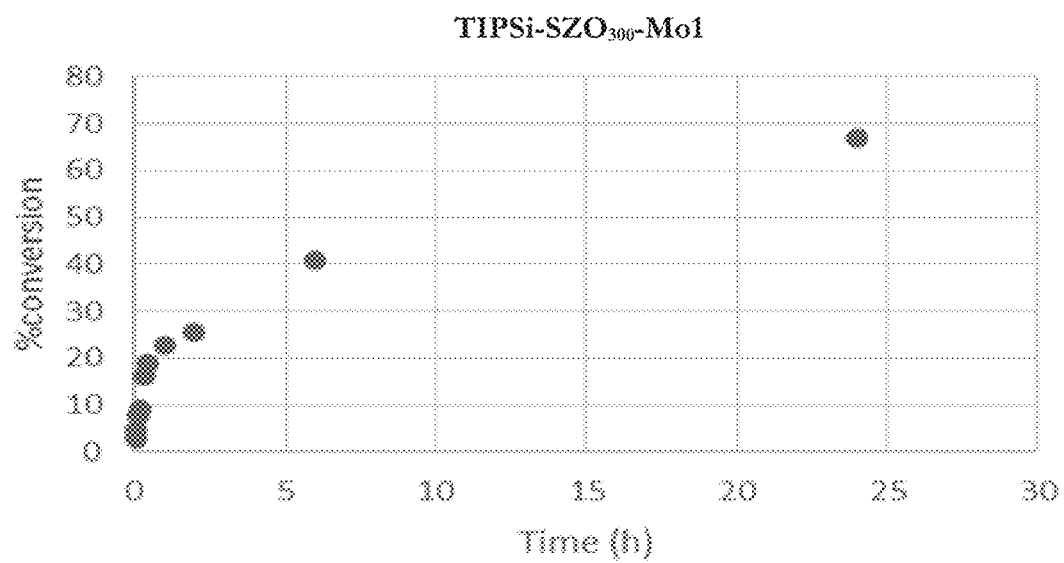
FIG. 24 shows a plot illustrating the percentage conversion as a function of time for the exemplary organosilicon complex TIPSi-SZO$_{300}$-Mo1 in accordance with the present disclosure.

FIG. 24 shows a plot illustrating the percentage conversion as a function of time for TIPSi-SZO$_{300}$-Mo1.

The above results confirm the reactivity of the TIPSi-SZO$_{300}$-Mo in the formation of homocoupled olefin as will be understood by a skilled person.

The Examples above show that electrophilic R$_3$Si$^+$ sites can be formed on oxide surfaces. The Examples also show that not all oxides are capable of forming these sites. Oxides promoting the formation of weakly coordinating ion pairs, which are present on SZO, form R$_3$Si$^+$ species that are active in HDF. Oxides that promote a formation of R$_3$Si—O$_x$, such as silica and alumina, are not active in HDF because R$_3$Si$^+$ sites are not formed. Though [TIPS][SZO] sites in 1 are very active in C—F bond activation, they are unreactive towards sp$^2$ C—F bonds and the C—F bonds in perfluorohexane. Further optimization of the interactions in R$_3$Si.O$_x$ may result in more reactive R$_3$Si$^+$ sites on oxides to activate these substrates.

The examples set forth above are provided to give those of ordinary skill in the art a complete disclosure and description of how to make and use the embodiments of multimetallic organometallic complexes, and related polymers, methods and systems of the disclosure, and are not intended to limit the scope of what the Applicants regard as their disclosure. Modifications of the above-described modes for carrying out the disclosure can be used by persons of skill in the art, and are intended to be within the scope of the following claims.

The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The term "alkyl" as used herein refers to a linear, branched, or cyclic saturated hydrocarbon group typically although not necessarily containing 1 to about 15 carbon atoms, or 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 15 carbon atoms. The term "cycloalkyl" intends a cyclic alkyl group, typically having 4 to 8, or 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl"

include linear, branched, cyclic, unsubstituted, substituted, and/or heteroatom-containing alkyl and lower alkyl, respectively.

The term "heteroatom-containing" as in a "heteroatom-containing alky group" refers to an alkyl group in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 24 carbon atoms, or aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The terms "cyclic", "cyclo-", and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo", "halogen", and "halide" are used in the conventional sense to refer to a chloro, bromo, fluoro or iodo substituent or ligand.

The term "olefins" as used herein indicates two carbons covalently bound to one another that contain a double bond (sp2-hybridized bond) between them. The other functional groups bound to each of these two carbons can be, for example, additional carbons, hydrogen atoms, or heteroatoms. The term terminal olefin as used herein refers to an organic compound which contains a carbon-carbon double bond of a methylene group (═CH2).

In some embodiments, the terminal olefin can be an olefin of formula CxH2x, wherein x is 3 to 20. Particularly, in some embodiments, a terminal olefin can be propene, 1-butene, 1-pentene, 1-hexene, 1-heptene, 1-octene, 1-nonene or 1,9-decadiene.

The term terminal diolefin as used herein refers to an organic compound which contains at least two carbon-carbon double bonds of a methylene group (═CH2). Particularly, in some embodiments, a terminal diolefin can be propene, butadiene, 1,4-pentadiene, 1,5-hexadiene, 1,6-heptadiene, 1,7-octadiene, 1,8-nonadiene or 1,9-decadiene.

The term cyclic olefin as used herein refers to an organic compound containing at least one carbon-carbon double bond in an aliphatic ring structure. In some embodiments, the aliphatic ring structure may contain one to three heteroatoms. Exemplary cyclic olefin includes cyclobutene, cyclopentene, cyclohexene, cycloheptene, cyclooctene, cyclononane, cyclodecene, 8,9,10-trinorborn-2-ene (norbornene) or 1,2,3,4,4a,5,8,8a-octahydro-1,4:5,8-dimethanonaphthalene (tetracyclododecene).

The term alkylene as used herein refers to an alkanediyl group which is a divalent saturated aliphatic group, with two carbon atoms as points of attachment, a linear or branched, cyclo, cyclic or acyclic structure. Exemplary alkylene includes propane-1,2-diyl group (—CH(CH3)CH2-) or propane-1,3-diyl group (—CH2CH2CH2-).

The term alkenylene refers to alkenediyl group which is a divalent unsaturated aliphatic group, with two carbon atoms as points of attachment, a linear or branched, cyclo, cyclic or acyclic structure, at least one nonaromatic carbon-carbon double bond. Exemplary alkylene includes 2-butene-1,4-diyl group (—CH2CH═CHCH2-).

The term alkynylene refers to alkynediyl group which is a divalent unsaturated aliphatic group, with two carbon atoms as points of attachment, a linear or branched, cyclo, cyclic or acyclic structure, at least one nonaromatic carbon-carbon triple bond. Exemplary alkylene includes 2-butyne-1,4-diyl group (—CH2C≡CCH2-).

The term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents.

Examples of such substituents include, without limitation: functional groups such as halo, hydroxyl, sulfhydryl, C1-C24 alkoxy, C2-C24 alkenyloxy, C2-C24 alkynyloxy, C5-C24 aryloxy, C6-C24 aralkyloxy, C6-C24 alkaryloxy, acyl (including C2-C24 alkylcarbonyl (—CO-alkyl) and C6-C24 arylcarbonyl (—CO-aryl)), acyloxy (—O-acyl, including C2-C24 alkylcarbonyloxy (—O—CO-alkyl) and C6-C24 arylcarbonyloxy (—O—CO-aryl)), C2-C24 alkoxycarbonyl (—(CO)—O-alkyl), C6-C24 aryloxycarbonyl (—(CO)—O-aryl), halocarbonyl (—(CO)—X where X is halo), C2-C24 alkylcarbonato (—O—(CO)—O-alkyl), C6-C24 arylcarbonato (—O—(CO)—O-aryl), carboxy (—COOH), carboxylato (COO$^-$), carbamoyl (—(CO)—NH2), mono-(C1-C24 alkyl)-substituted carbamoyl (—(CO)—NH(C1-C24 alkyl)), di-(C1-C24 alkyl)-substituted carbamoyl (—(CO)—N(C1-C24 alkyl)2), mono-(C5-C24 aryl)-substituted carbamoyl (—(CO)—NH-aryl), di-(C5-C24 aryl)-substituted carbamoyl (—(CO)—N(C5-C24 aryl)2), di-N—(C1-C24 alkyl),N—(C5-C24 aryl)-substituted carbamoyl, thiocarbamoyl (—(CS)—NH2), mono-(C1-C24 alkyl)-substituted thiocarbamoyl (—(CO)—NH (C1-C24 alkyl)), di-(C1-C24 alkyl)-substituted thiocarbamoyl (—(CO)—N(C1-C24 alkyl)2), mono-(C5-C24 aryl)-substituted thiocarbamoyl (—(CO)—NH-aryl), di-(C5-C24 aryl)-substituted thiocarbamoyl (—(CO)—N(C5-C24 aryl)2), di-N—(C1-C24 alkyl),N—(C5-C24 aryl)-substituted thiocarbamoyl, carbamido (—NH—(CO)—NH2), cyano(—C≡N), cyanato (—O—C≡N), thiocyanato (—S—C≡N), formyl (—(CO)—H), thioformyl ((CS)—H), amino (—NH2), mono-(C1-C24 alkyl)-substituted amino, di-(C1-C24 alkyl)-substituted amino, mono-(C5-C24 aryl)-substituted amino, di-(C5-C24 aryl)-substituted amino, C2-C24 alkylamido (—NH—(CO)-alkyl), C6-C24 arylamido (—NH—(CO)-aryl), imino (—CR=NH where R=hydrogen, C1-C24 alkyl, C5-C24 aryl, C6-C24 alkaryl, C6-C24 aralkyl, etc.), C2-C20 alkylimino (CR=N(alkyl), where R=hydrogen, C1-C24 alkyl, C5-C24 aryl, C6-C24 alkaryl, C6-C24 aralkyl, etc.), arylimino (—CR=N(aryl), where R=hydrogen, C1-C20 alkyl, C5-C24 aryl, C6-C24 alkaryl, C6-C24 aralkyl, etc.), nitro (—NO2), nitroso (—NO), sulfo (—SO2-OH), sulfonato (—SO2-O⁻), C1-C24 alkylsulfanyl (—S-alkyl; also termed "alkylthio"), C5-C24 arylsulfanyl (—S-aryl; also termed "arylthio"), C1-C24 alkylsulfinyl (—(SO)-alkyl), C5-C24 arylsulfinyl (—(SO)-aryl), C1-C24 alkylsulfonyl (—SO2-alkyl), C5-C24 arylsulfonyl (—SO2-aryl), boryl (—BH2), borono (—B(OH)2), boronato (—B(OR)2 where R is alkyl or other hydrocarbyl), phosphono (—P(O)(OH)2), phosphonato (—P(O)(O⁻)2), phosphinato (—P(O)(O⁻), phospho (—PO2), phosphino (—PH2), silyl (—SiR3 wherein R is hydrogen or hydrocarbyl), and silyloxy (—O-silyl); and the hydrocarbyl moieties C1-C24 alkyl (e.g. C1-C12 alkyl and C1-C6 alkyl), C2-C24 alkenyl (e.g. C2-C12 alkenyl and C2-C6 alkenyl), C2-C24 alkynyl (e.g. C2-C12 alkynyl and C2-C6 alkynyl), C5-C24 aryl (e.g. C5-C14 aryl), C6-C24 alkaryl (e.g. C6-C16 alkaryl), and C6-C24 aralkyl (e.g. C6-C16 aralkyl).

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The term "alkaryl" refers to an aryl group with an alkyl substituent, and the term "aralkyl" refers to an alkyl group with an aryl substituent, wherein "aryl" and "alkyl" are as defined above. In some embodiments, alkaryl and aralkyl groups contain 6 to 24 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "Periodic Table" refers to the version of IUPAC Periodic Table of the Elements dated Nov. 28, 2016, which is accessible at iupac.org/wp-content/uploads/2015/07/IUPAC_Periodic_Table-28Nov16.pdf.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In summary, in several embodiments, described herein are organosilicon compound, related complex that allow performance of fluorocarbon compound or olefin-based reactions and in particular polymerization of olefins to produce polyolefin polymers, and related methods and systems are described.

In particular, it will be understood that various modifications may be made without departing from the spirit and scope of the present disclosure. Accordingly, other embodiments are within the scope of the following claims.

REFERENCES

1. Ahrens, M.; Scholz, G.; Braun, T.; Kemnitz, E. Angew. Chem. Int. Ed. 2013, 52, 5328-5332; Angew. Chem. 2013, 125, 5346-5440.

2. Beckett, M. A.; Brassington, D. S.; Coles, S. J.; Hursthouse, M. B. Inorg. Chem. Commun. 2000, 3, 530-533.
3. Comas-Vives, A.; Schwarzwalder, M.; Copéret, C.; Sautet, P. J. Phys. Chem. C 2015, 119, 7156-7163.
4. Comas-Vives, A.; Valla, M.; Copéret, C.; Sautet, P. ACS Cent. Sci. 2015, 1, 313-319.
5. Conley, M. P.; Copéret, C.; Thieuleux, C. ACS Catal. 2014, 4, 1458-1469; b) Zapilko, C.; Anwander, R. Chem. Mater. 2006, 18, 1479-1482.
6. Conley, M. P.; Delley, M. F.; Nunez-Zarur, F.; Comas-Vives, A.; Copéret, C. Inorg. Chem. 2015, 54, 5065-5078.
7. Conley, M. P.; Delley, M. F.; Siddiqi, G.; Lapadula, G.; Norsic, S.; Monteil, V.; Safonova, O. V.; Copéret, C. Angew. Chem. Int. Ed. 2014, 53, 1872-1876; Angew. Chem. 2014, 126, 1903-1907.
8. Coperet, C. Chem. Rev. 2010, 110, 656-680.
9. Copéret, C.; Comas-Vives, A.; Conley, M. P.; Estes, D. P.; Fedorov, A.; Mougel, V.; Nagae, H.; Núñez-Zarur, F.; Zhizhko, P. A. Surface Organometallic and Coordination Chemistry toward Single-Site Heterogeneous Catalysts: Strategies, Methods, Structures, and Activities. Chem. Rev. 2016, 116, 323-421.
10. Corma, A.; Garcia, H. Chem. Rev. 2003, 103, 4307-4366; b) Roman-Leshkov, Y.; Davis, M. E. ACS Catal. 2011, 1, 1566-1580.
11. Culver, D. B.; Tafazolian, H.; Conley, M. P. Organometallics 2018.
12. Delley, M. F.; Lapadula, G.; Núñez-Zarur, F.; Comas-Vives, A.; Kalendra, V.; Jeschke, G.; Baabe, D.; Walter, M. D.; Rossini, A. J.; Lesage, A.; Emsley, L.; Maury, O.; Copéret, C. J. Am. Chem. Soc. 2017, 139, 8855-8867.
13. Delley, M. F.; Nunez-Zarur, F.; Conley, M. P.; Comas-Vives, A.; Siddiqi, G.; Norsic, S.; Monteil, V.; Safonova, O. V.; Copéret, C. Proc. Nat. Acad. Sci. USA 2014, 111, 11624-11629.
14. Douvris, C.; Nagaraja, C. M.; Chen, C. H.; Foxman, B. M.; Ozerov, O. V. J. Am. Chem. Soc. 2010, 132, 4946-4953.
15. Douvris, C.; Ozerov, O. V. Science 2008, 321, 1188-1190.
16. Duttwyler, S.; Douvris, C.; Fackler, N. L. P.; Tham, F. S.; Reed, C. A.; Baldridge, K. K.; Siegel, J. S. Angew. Chem. Int. Ed. 2010, 49, 7519-7522; Angew. Chem. 2010, 122, 7681-7684.
17. Großekappenberg, H.; Reißmann, M.; Schmidtmann, M.; Müller, T. Organometallics 2015, 34, 4952-4958.
18. Gu, W.; Stalzer, M. M.; Nicholas, C. P.; Bhattacharyya, A.; Motta, A.; Gallagher, J. R.; Zhang, G.; Miller, J. T.; Kobayashi, T.; Pruski, M.; Delferro, M.; Marks, T. J. J. Am. Chem. Soc. 2015, 137, 6770-6780.
19. Hu, B.; Bean, Getsoian, A.; Schweitzer, N. M.; Das, U.; Kim, H.; Niklas, J.; Poluektov, O.; Curtiss, L. A.; Stair, P. C.; Miller, J. T.; Hock, A. S. J. Catal. 2015, 322, 24-37.
20. Kemnitz, E.; Gross, U.; Rudiger, S.; Shekar, C. S. Angew. Chem. Int. Ed. 2003, 42, 4251-4254; Angew. Chem. 2003, 115, 4383-4386; c) Krahl, T.; Kemnitz, E. Cat. Sci. Tech. 2017, 7, 773-796.
21. Klare, H. F. T.; Oestreich, M. Dalton Trans. 2010, 39, 9176-9184; b) Susanne, B.; Martin, O. Angew. Chem. Int. Ed. 2017, 56, 52-59.
22. Klet, R. C.; Kaphan, D. M.; Liu, C.; Yang, C.; Kropf, A. J.; Perras, F. A.; Pruski, M.; Hock, A. S.; Delferro, M. J. Am. Chem. Soc. 2018, 140, 6308-6316.
23. Liberman-Martin, A. L.; Bergman, R. G.; Tilley, T. D. J. Am. Chem. Soc. 2015, 137, 5328-5331.
24. Mayer, U.; Gutmann, V.; Gerger, W. Monatsh. Chem. 1975, 106, 1235-1257.
25. Olah, G. A., and Watkins, M. Fluorinations with Pyridinium Polyhydrogen Fluoride Reagent: 1-Fluoroadamantane. Org. Synth. 1978, 58, 75.
26. Osegovic, J. P.; Drago, R. S. J. Catal. 1999, 182, 1-4.
27. Reed, C. A. Acc. Chem. Res. 1998, 31, 325-332; b) Reed, C. A. Acc. Chem. Res. 2010, 43, 121-128.
28. Rezisha, M.; Marcel, S.; Claudia, L.; Lutz, G. Angew. Chem. Int. Ed. 2018, 57, 1717-1720.
29. Sattler, J. J. H. B.; Ruiz-Martinez, J.; Santillan-Jimenez, E.; Weckhuysen, B. M. Chem. Rev. 2014.
30. Schweitzer, N. M.; Hu, B.; Das, U.; Kim, H.; Greeley, J.; Curtiss, L. A.; Stair, P. C.; Miller, J. T.; Hock, A. S. ACS Catal. 2014, 4, 1091-1098.
31. Scott, V. J.; Celenligil-Cetin, R.; Ozerov, O. V. J. Am. Chem. Soc. 2005, 127, 2852-2853.
32. Searles, K.; Siddiqi, G.; Safonova, O. V.; Copéret, C. Chem. Sci. 2017, 8, 2661-2666.
33. Shao, B.; Bagdasarian, A. L.; Popov, S.; Nelson, H. M. Science 2017, 355, 1403-1407.
34. Stalzer, M.; Delferro, M.; Marks, T. Catal. Lett. 2015, 145, 3-14.
35. Stalzer, M. M.; Nicholas, C. P.; Bhattacharyya, A.; Motta, A.; Delferro, M.; Marks, T. J. Angew. Chem. Int. Ed. 2016, 55, 5263-5267; Angew. Chem. 2016, 128, 5349-5353
36. Tafazolian, H.; Culver, D. B.; Conley, M. P. A Well-Defined Ni(II) α-Diimine Catalyst Supported on Sulfated Zirconia for Polymerization Catalysis. Organometallics 2017, 36, 2385-2388.
37. Valla, M.; Wischert, R.; Comas-Vives, A.; Conley, M. P.; Verel, R.; Copéret, C.; Sautet, P. J. Am. Chem. Soc. 2016, 138, 6774-6785.
38. Williams, L. A.; Guo, N.; Motta, A.; Delferro, M.; Fragala, I. L.; Miller, J. T.; Marks, T. J. Proc. Nat. Acad. Sci. USA 2013, 110, 413-418.
39. Wischert, R.; Copéret, C.; Delbecq, F.; Sautet, P., Angew. Chem. Int. Ed. 2011, 50, 3202-3205; Angew. Chem. 2011, 123, 3260-3263.
40. Wischert, R.; Coperet, C.; Delbecq, F.; Sautet, P. Chem. Comm. 2011, 47, 4890-4892.
41. Wischert, R.; Laurent, P.; Copéret, C.; Delbecq, F.; Sautet, P. J. Am. Chem. Soc. 2012, 134, 14430-14449.
42. Xie, Z.; Manning, J.; Reed, R. W.; Mathur, R.; Boyd, P. D. W.; Benesi, A.; Reed, C. A. J. Am. Chem. Soc. 1996, 118, 2922-2928.
43. Zapilko, C.; Anwander, R. Chem. Mater. 2006, 18, 1479-1482.

The invention claimed is:

1. A solid organosilicon compound comprising a Formula (I)

$$[M^1{}_mO_{o1}Si^1(R^1R^2R^3)L_{q/z}] [M^2{}_nO_{o2}Si^2(R^1R^2R^3)]_x \quad (I)$$

wherein
$M^1$ and $M^2$ are selected from the group consisting of Al, Zn, and Zr, and any combinations thereof-having an oxidation state of +p, wherein p ranges from 2 to 4,
$Si^1$ is a Lewis acidic silicon connected to $M^1$ via an oxygen, wherein other atoms in the solid organosilicon compound are represented stoichiometrically in relation to $Si^1$,
q represents a charge for $M^1{}_mO_{o1}Si^1(R^1R^2R^3)$, wherein q ranges from 1 to 3,
L is selected from the group consisting of sulfate ($SO_4{}^{2-}$), sulfite ($SO_3{}^{2-}$), selenate ($SeO_4{}^{2-}$), phosphonate ($HPO_3{}^{2-}$), phosphate ($PO_4{}^{3-}$), pyrophosphate ($P_2O_7{}^{4-}$), chloride ($Cl^-$), chlorate ($ClO_3{}^-$), bromide (Br), bromate ($BrO_3{}^-$), tetraborate ($B_4O_7{}^{2-}$), vanadate ($VO_4^{3-}$), tungstate ($WO_4^{2-}$), molybdate ($MoO_4^{2-}$), p-toluene sulfonate, trifluoroacetate and any combinations thereof and has a negative charge of –z, wherein z ranges from 1 to 3, $Si^2$ represents a silicon bounded to $M^2$ via an oxygen, m is number of $M^1$, o1, and o2 are the number of O respectively bonded to $M^1$ and $M^2$, wherein $(m \times p)+[o1 \times (-2)]+1=q$, q/z is the number of counter anion L, $p+[o2 \times (-2)]+1=0$, $R^1$, $R^2$, and $R^3$ are each independent a substituent comprising 1 to 24 carbon atoms, x ranges from 0 to 1000.

2. The solid organosilicon compound of claim 1, wherein $M^1$ and $M^2$ are Zr.

3. The solid organosilicon compound of claim 1, wherein L is sulfate ($SO_4^{2-}$).

4. The solid organosilicon compound of claim 1, wherein x ranges from 0.05 to 10.

5. The solid organosilicon compound of claim 1, wherein m ranges from 10 to 1000.

6. The solid organosilicon compound of claim 1, wherein $M^1$ and $M^2$ are Zr having an oxidation state of +4,
L is a sulfate anion bounded to $M^1$,
$Si^2$ is at least two atoms spaced apart from an oxygen of the sulfate anion,
m ranges from 10 to 1000,
x ranges from 0.05 to 10.

7. A catalytic system for hydrodefluorination (HDF) of a fluorocarbon compound, the catalytic system comprising
a solid organosilicon compound of Formula (I) as defined in claim 1,
a fluorocarbon compound and
a silane compound comprising at least one Si—H group.

8. The solid organosilicon compound of claim 1, wherein:
$M^1$ and $M^2$ are each Zr,
q is 2,
p is 4,
L is sulfate ($SO_4^{2-}$),
m is 100,
o1 is 399/2 and o2 is 5/2,
$R^1$, $R^2$, and $R^3$ are each independent isopropyl, and
x is 10.

9. The catalytic system for hydrodefluorination (HDF) of claim 7, wherein the fluorocarbon includes at least one $sp^3$ C—F bond.

10. The catalytic system for hydrodefluorination (HDF) of claims 7, wherein the fluorocarbon is represented by Formula (XI)

$$C_nH_{2n+2-s}F_s \qquad (XI)$$

wherein
n ranges from 1 to 30, and
s ranges from 1 to 2n.

11. The catalytic system for hydrodefluorination (HDF) of claim 7, wherein the fluorocarbon is benzotrifluoride, octofluorotoluene, or 1-fluoroadamatane.

12. The catalytic system for hydrodefluorination (HDF) of claim 7, wherein the fluorocarbon is represented by Formula (XII)

$$R''F \qquad (XII)$$

wherein
R" is selected from the group consisting of a linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl group.

13. The catalytic system of any 7, wherein the silane compound is selected from the group consisting of triethylsilane, diethylmethylsilane, polymethylhydrosilane (PMHS), methyldiethoxysilane, diethoxydimethylsilane triethoxysilane.

14. A method for hydrodefluorination (HDF) of a fluorocarbon compound, the method comprises
contacting a solid organosilicon compound of Formula (I) as defined in claim 1 with the fluorocarbon compound,
the contacting performed in presence of a silane compound comprising at least one Si—H group for a time and under condition to allow hydrodefluorination of the fluorocarbon compound.

15. A method for preparing a solid organosilicon compound of Formula (I) as defined in claim 1, the method comprises contacting a solid oxide of Formula (IV)

$$[M^1{}_mHO_{o1}L_{q/z}][M^2HO_{o2}]_x \qquad (IV)$$

with a silane of Formula (V)

$$SiR^1R^2R^3R^4 \qquad (V)$$

wherein
$M^1$ and $M^2$ are an element having an oxidation state of +p,
L is a counter anion bounded to $M^1$ and has a negative charge of –z,
m is number of $M^1$,
o1, and o2 the number of O respectively bonded to $M^1$ and $M^2$, $(m \times p)+[o1 \times (-2)]+1=q$, q/z is the number of counter anion L, $p+[o2 \times (-2)]+1=0$, $R^1$, $R^2$, $R^3$, and $R^4$ are each independent a substituent comprising 1 to 24 carbon atoms, an isopropyl, an allyl group, a chloride, a bromide, an iodide, or a triflate,
x ranges from 0 to 1000
for a time and under condition to form an organosilicon compound Formula (I).

16. The method of claim 15, wherein
$M^1$ and $M^2$ are Mo having an oxidation state of +4,
L is a sulfate anion bounded to $M^1$ and has a negative charge of –2,
$R^1$, $R^2$, and $R^3$ are each isopropyl group.

* * * * *